(12) United States Patent
Stokes et al.

(10) Patent No.: US 7,722,628 B2
(45) Date of Patent: May 25, 2010

(54) DEVICE FOR PLICATING AND FASTENING GASTRIC TISSUE

(75) Inventors: Michael J. Stokes, Cincinnati, OH (US); Mark S. Zeiner, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 448 days.

(21) Appl. No.: 11/696,222

(22) Filed: Apr. 4, 2007

(65) Prior Publication Data
US 2008/0249541 A1   Oct. 9, 2008

(51) Int. Cl.
A61B 17/10 (2006.01)
(52) U.S. Cl. .................................... 606/142
(58) Field of Classification Search ............ 606/213, 606/216, 142–143; 600/37, 565; 607/128
See application file for complete search history.

(56) References Cited

U.S. PATENT DOCUMENTS

| | | | |
|---|---|---|---|
| 4,643,178 A * | 2/1987 | Nastari et al. ................. | 606/74 |
| 5,152,790 A * | 10/1992 | Rosenberg et al. ....... | 623/13.14 |
| 5,156,616 A * | 10/1992 | Meadows et al. .......... | 606/232 |
| 5,320,629 A * | 6/1994 | Noda et al. ................. | 606/139 |
| 5,336,231 A * | 8/1994 | Adair .......................... | 606/148 |
| 5,374,278 A * | 12/1994 | Chesterfield et al. ....... | 606/228 |
| 5,454,823 A * | 10/1995 | Richardson et al. ......... | 606/148 |
| 5,486,197 A * | 1/1996 | Le et al. ..................... | 606/232 |
| 5,527,322 A * | 6/1996 | Klein et al. ................. | 606/144 |
| 5,582,616 A | 12/1996 | Bolduc et al. | |
| 5,626,585 A | 5/1997 | Mittelstadt et al. | |
| 5,643,295 A * | 7/1997 | Yoon .......................... | 606/151 |
| 5,674,230 A * | 10/1997 | Tovey et al. ................. | 606/139 |
| 5,715,987 A | 2/1998 | Kelley et al. | |
| 6,125,852 A | 10/2000 | Stevens et al. | |
| 6,228,098 B1 | 5/2001 | Kayan et al. | |
| 6,277,131 B1 | 8/2001 | Kalikow | |
| 6,306,149 B1 | 10/2001 | Meade | |
| 6,330,964 B1 | 12/2001 | Kayan et al. | |
| 6,352,541 B1 | 3/2002 | Kienzle et al. | |
| 6,383,198 B1 | 5/2002 | Hamilton | |
| 6,432,115 B1 * | 8/2002 | Mollenauer et al. ......... | 606/148 |
| 6,450,391 B1 | 9/2002 | Kayan et al. | |

(Continued)

FOREIGN PATENT DOCUMENTS

WO    WO 02/35980 A2    5/2002

(Continued)

OTHER PUBLICATIONS

European Search Report re: EP08251296 dated Aug. 27, 2008.

(Continued)

*Primary Examiner*—Darwin P Erezo
*Assistant Examiner*—Son Dang

(57) ABSTRACT

A device for maintaining a plication within a hollow organ. The device includes an elongated member having distal and proximal ends. The distal end is for insertion into a body cavity. The elongated member has an end effector at its distal end. The end effector has an outer cylinder having at least one opening, and an inner cylinder having at least one opening. The inner cylinder is at least partially disposed within the outer cylinder and the cylinders are rotatable with respect to each other. The end effector is detachable from the elongated member such that it can remain within the body cavity.

7 Claims, 23 Drawing Sheets

U.S. PATENT DOCUMENTS

| | | | |
|---|---|---|---|
| 6,558,400 | B2 | 5/2003 | Deem et al. |
| 6,656,194 | B1 | 12/2003 | Gannoe et al. |
| 6,663,639 | B1 | 12/2003 | Laufer et al. |
| 6,695,854 | B1 | 2/2004 | Kayan et al. |
| 6,716,226 | B2 | 4/2004 | Sixto, Jr. et al. |
| 6,740,098 | B2 | 5/2004 | Abrams et al. |
| 6,746,460 | B2 | 6/2004 | Gannoe et al. |
| 6,770,076 | B2 * | 8/2004 | Foerster .................. 606/326 |
| 6,773,440 | B2 * | 8/2004 | Gannoe et al. .............. 606/142 |
| 6,773,441 | B1 | 8/2004 | Laufer et al. |
| 6,773,450 | B2 * | 8/2004 | Leung et al. ................ 606/232 |
| 6,776,783 | B1 * | 8/2004 | Frantzen et al. ............ 606/151 |
| 6,790,214 | B2 | 9/2004 | Kraemer et al. |
| 6,835,200 | B2 | 12/2004 | Laufer et al. |
| 6,837,895 | B2 | 1/2005 | Mayenberger |
| 6,923,824 | B2 * | 8/2005 | Morgan et al. .............. 606/232 |
| 6,994,715 | B2 * | 2/2006 | Gannoe et al. .............. 606/153 |
| 7,059,509 | B2 | 6/2006 | Brown |
| 7,083,629 | B2 | 8/2006 | Weller et al. |
| 7,083,630 | B2 | 8/2006 | DeVries et al. |
| 7,090,690 | B2 * | 8/2006 | Foerster et al. ............. 606/232 |
| 7,097,650 | B2 | 8/2006 | Weller et al. |
| 7,153,312 | B1 | 12/2006 | Torrie et al. |
| 7,175,638 | B2 | 2/2007 | Gannoe et al. |
| 7,179,265 | B2 | 2/2007 | Manetakis et al. |
| 7,306,614 | B2 * | 12/2007 | Weller et al. ................ 606/151 |
| 7,320,692 | B1 | 1/2008 | Bender et al. |
| 7,344,544 | B2 | 3/2008 | Bender et al. |
| 7,390,328 | B2 * | 6/2008 | Modesitt .................... 606/144 |
| 7,458,978 | B1 | 12/2008 | Bender et al. |
| 7,473,252 | B2 * | 1/2009 | Barry .......................... 606/41 |
| 7,473,258 | B2 | 1/2009 | Clauson et al. |
| 2002/0068946 | A1 * | 6/2002 | Kortenbach et al. ......... 606/142 |
| 2002/0082621 | A1 * | 6/2002 | Schurr et al. ................ 606/151 |
| 2002/0183768 | A1 | 12/2002 | Deem et al. |
| 2004/0006351 | A1 | 1/2004 | Gannoe et al. |
| 2004/0044354 | A1 | 3/2004 | Gannoe et al. |
| 2004/0059347 | A1 | 3/2004 | Hamilton |
| 2004/0088008 | A1 | 5/2004 | Gannoe et al. |
| 2004/0098050 | A1 * | 5/2004 | Foerster et al. ............. 606/232 |
| 2004/0122452 | A1 | 6/2004 | Deem et al. |
| 2004/0122453 | A1 | 6/2004 | Deem et al. |
| 2004/0162568 | A1 | 8/2004 | Saadat et al. |
| 2004/0167546 | A1 | 8/2004 | Saadat et al. |
| 2004/0225183 | A1 | 11/2004 | Michlitsch et al. |
| 2005/0033363 | A1 | 2/2005 | Bojarski et al. |
| 2005/0070931 | A1 | 3/2005 | Li et al. |
| 2005/0075654 | A1 | 4/2005 | Kelleher |
| 2005/0080438 | A1 | 4/2005 | Weller et al. |
| 2005/0085830 | A1 | 4/2005 | Lehman et al. |
| 2005/0149072 | A1 | 7/2005 | DeVries et al. |
| 2005/0177176 | A1 | 8/2005 | Gerbi et al. |
| 2005/0177180 | A1 | 8/2005 | Kaganov et al. |
| 2005/0192599 | A1 | 9/2005 | Demarais |
| 2005/0192601 | A1 | 9/2005 | Demarais |
| 2005/0216040 | A1 | 9/2005 | Gertner et al. |
| 2005/0222592 | A1 | 10/2005 | Gannoe et al. |
| 2005/0228415 | A1 | 10/2005 | Gertner |
| 2005/0245945 | A1 | 11/2005 | Ewers et al. |
| 2005/0251160 | A1 | 11/2005 | Saadat et al. |
| 2005/0256533 | A1 | 11/2005 | Roth et al. |
| 2006/0009789 | A1 | 1/2006 | Gambale et al. |
| 2006/0044837 | A1 | 3/2006 | Lee |
| 2006/0142787 | A1 | 6/2006 | Weller et al. |
| 2006/0264984 | A1 | 11/2006 | Schurr et al. |
| 2006/0287661 | A1 | 12/2006 | Bolduc et al. |
| 2007/0060922 | A1 * | 3/2007 | Dreyfuss ..................... 606/72 |
| 2007/0093861 | A1 | 4/2007 | Vardi |
| 2007/0112942 | A1 | 5/2007 | Moquin et al. |
| 2007/0185504 | A1 | 8/2007 | Manetakis et al. |
| 2009/0072006 | A1 | 3/2009 | Clauson et al. |
| 2009/0134198 | A1 | 5/2009 | Knodel et al. |

FOREIGN PATENT DOCUMENTS

| | | |
|---|---|---|
| WO | WO 02/096327 | 12/2002 |
| WO | WO 02/096327 A2 | 12/2002 |
| WO | WO 2004/004542 A2 | 1/2004 |
| WO | WO 2004/014237 A1 | 2/2004 |
| WO | WO 2004/019765 A2 | 3/2004 |
| WO | WO 2004/037064 A2 | 5/2004 |

OTHER PUBLICATIONS

EPO Search Report dated Jul. 7, 2008 for European Patent Application No. EP 08 25 1294.

* cited by examiner

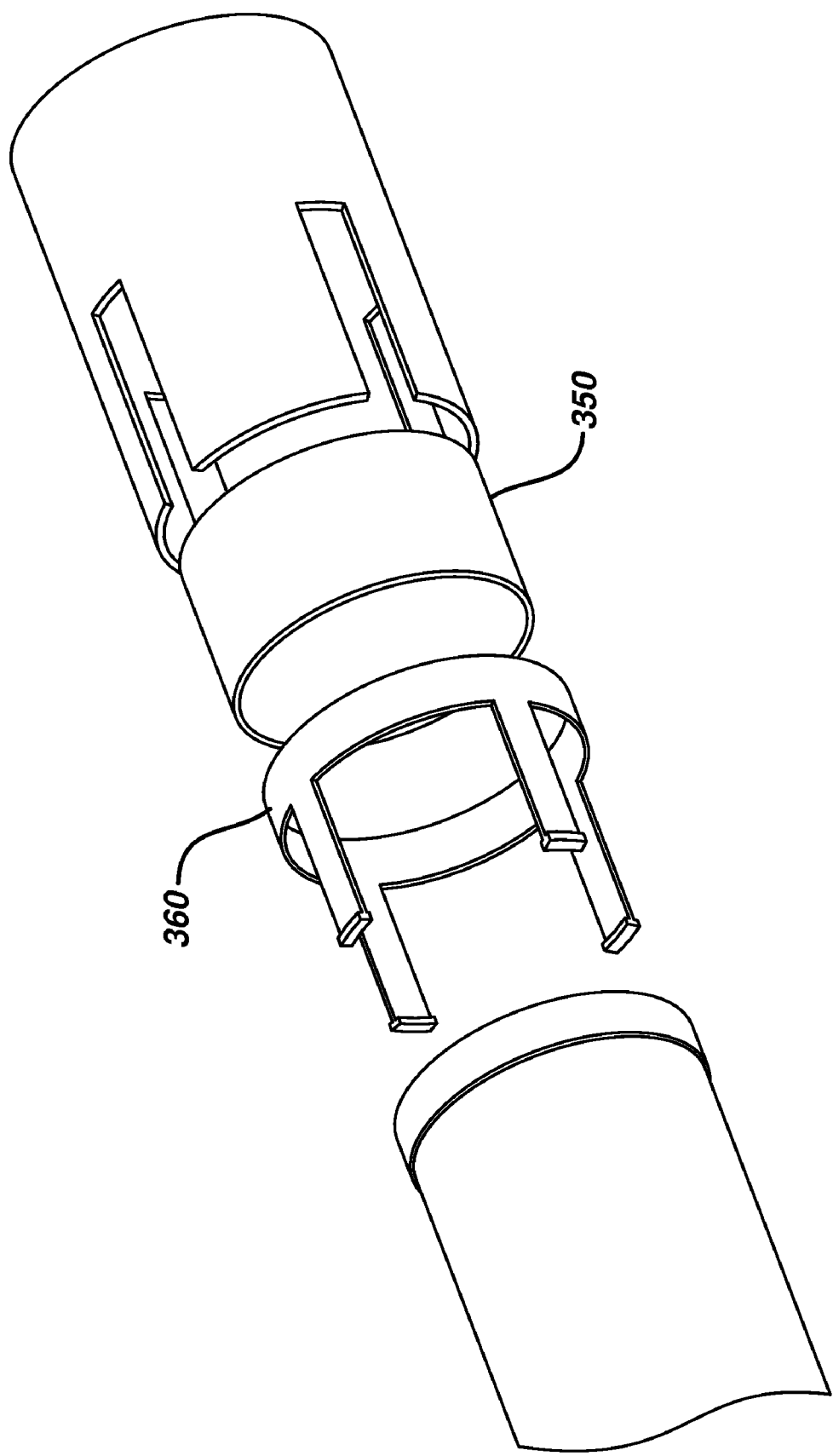

DEVICE FOR PLICATING AND FASTENING GASTRIC TISSUE

FIELD OF THE INVENTION

The present invention relates in general to a bariatric treatment device and, more particularly, to a device for transorally plicating and fastening areas of gastric tissue to achieve a gastric volume reduction.

BACKGROUND OF THE INVENTION

The percentage of the world's population suffering from morbid obesity is steadily increasing. Severely obese persons are susceptible to increased risk of heart disease, stroke, diabetes, pulmonary disease, and accidents. Because of the effect of morbid obesity to the life of the patient, methods of treating morbid obesity are being researched.

Numerous non-operative therapies for morbid obesity have been tried with virtually no permanent success. Dietary counseling, behavior modification, wiring a patient's jaws shut, and pharmacological methods have all been tried, and failed to correct the condition. Mechanical apparatuses for insertion into the body through non-surgical means, such as the use of gastric balloons to fill the stomach have also been employed in the treatment of the condition. Such devices cannot be employed over a long term, however, as they often cause severe irritation, necessitating their periodic removal and hence interruption of treatment. Thus, the medical community has evolved surgical approaches for treatment of morbid obesity.

Most surgical procedures for treatment of morbid obesity may generally be classified as either being directed toward the prevention of absorption of food (malabsorption), or restriction of stomach to make the patient feel full (gastric restriction) The most common malabsorption and gastric restriction technique is the gastric bypass. In variations of this technique, the stomach is horizontally divided into two isolated pouches, with the upper pouch having a small food capacity. The upper pouch is connected to the small intestine, or jejunum, through a small stoma, which restricts the processing of food by the greatly reduced useable stomach. Since food bypass much of the intestines, the amount of absorption of food is greatly reduced.

There are many disadvantages to the above procedure. Typically the above mentioned procedure is performed in an open surgical environment. Current minimally invasive techniques are difficult for surgeons to master, and have many additional drawbacks. Also, there is a high level of patient uneasiness with the idea of such a drastic procedure which is not easily reversible. In addition, all malabsorption techniques carry ongoing risks and side effects to the patient, including malnutrition and dumping syndrome.

Consequently, many patients and physicians prefer to undergo a gastric restriction procedure for the treatment of morbid obesity. One of the most common procedures involves the implantation of an adjustable gastric band.

Examples of an adjustable gastric band can be found in U.S. Pat. No. 4,592,339 issued to Kuzmak; RE 36176 issued to Kuzmak; U.S. Pat. No. 5,226,429 issued to Kuzmak; U.S. Pat. No. 6,102,922 issued to Jacobson and U.S. Pat. No. 5,601,604 issued to Vincent, all of which are hereby incorporated herein by reference. In accordance with current practice, a gastric band is operatively placed to encircle the stomach. This divides the stomach into two parts with a stoma in-between. An upper portion, or a pouch, which is relatively small, and a lower portion which is relatively large. The small partitioned portion of the stomach effectively becomes the patients new stomach, requiring very little food to make the patient feel full.

However, patients and physicians are seeking even more less invasive products and procedures for treating morbid obesity.

SUMMARY OF THE INVENTION

A device for maintaining a plication within a hollow organ. The device includes an elongated member having distal and proximal ends. The distal end is for insertion into a body cavity. The elongated member has an end effector at its distal end. The end effector has an outer cylinder having at least one opening, and an inner cylinder having at least one opening. The inner cylinder is at least partially disposed within the outer cylinder and the cylinders are rotatable with respect to each other. The end effector is detachable from the elongated member such that it can remain within the body cavity

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings, in which:

FIG. 24 is an exploded view of the embodiment shown in FIG. 22;

DETAILED DESCRIPTION OF THE INVENTION

The present invention pertains to an endoscopic tissue plicating and fastening device for forming tissue folds within a gastric cavity in order to reduce the volume of the cavity. By creating and securing a plurality of folds along the interior walls of the gastric cavity, the present invention reduces the surface area within the cavity, thereby reducing the available food volume in the stomach. The present invention provides a simplified tissue plicating procedure in which the tissue folds are retained by either staples, or absorbable or removable clips, thus enabling the procedure to be easily reversed. Additionally, the present invention enables large areas of the stomach cavity to be plicated transorally, thus providing an effective bariatric treatment without the trauma encountered in an open surgery plication procedure.

Figure 1:
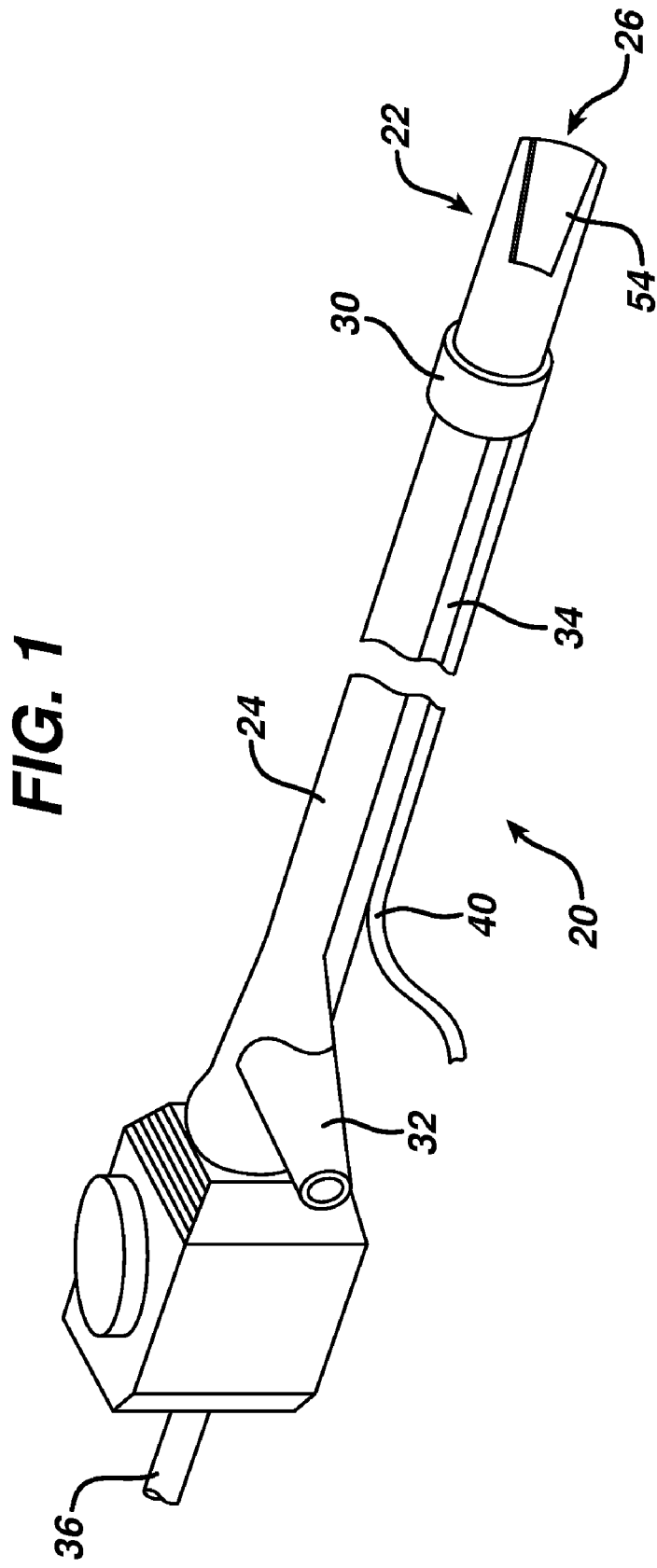
FIG. 1 is a perspective view of a first embodiment for the tissue plicating device of the present invention.

FIG. 1 illustrates a first embodiment for a tissue plicating device 20 of the present invention. Tissue plicating device 20 comprises a folding member or end effector 22 connected at the distal end of an elongated member such as a flexible endoscope 24. Folding member 22 includes an open distal end 26 for receiving tissue drawn into the device. A connecting member 30 extends between folding member 22 and endoscope 24 to securely attach the folding member to the endoscope, so that the folding member is transferred along with the endoscope during transoral insertion and removal. Endoscope 24 includes a side port 32 providing access to a working channel within the endoscope, as well as visualization capabilities for guiding device 20 to a desired location within a gastric cavity. Vacuum is provided to folding member 22 for drawing tissue into the device. In the embodiment shown in FIG. 1, vacuum is provided through a separate vacuum line 34, which extends along the exterior length of endoscope 24. Vacuum line 34 connects at a proximal end 36 to a conventional vacuum source (not shown). In an alternative embodiment, vacuum can be provided to folding member 22 through the working channel of endoscope 24, rather than through a separate exterior vacuum line.

Control of device 20 is provided through a connection 40 that extends along the exterior length of endoscope 24. Control connection 40 is attached at a distal end to folding member 22 for moving the member between an open and closed position, as will be described in more detail below. At a proximal end, control connection 40 attaches to a control assembly (not shown). The control assembly is operated by a surgeon in order to perform tissue folding and securing procedures. A number of different types of control assemblies may be utilized to drive the folding member of the present invention. These assemblies may include a push/pull cabling system, a rotational cable/rod, a hydraulic actuation system, or an electromagnetic actuation system.

Figure 2:
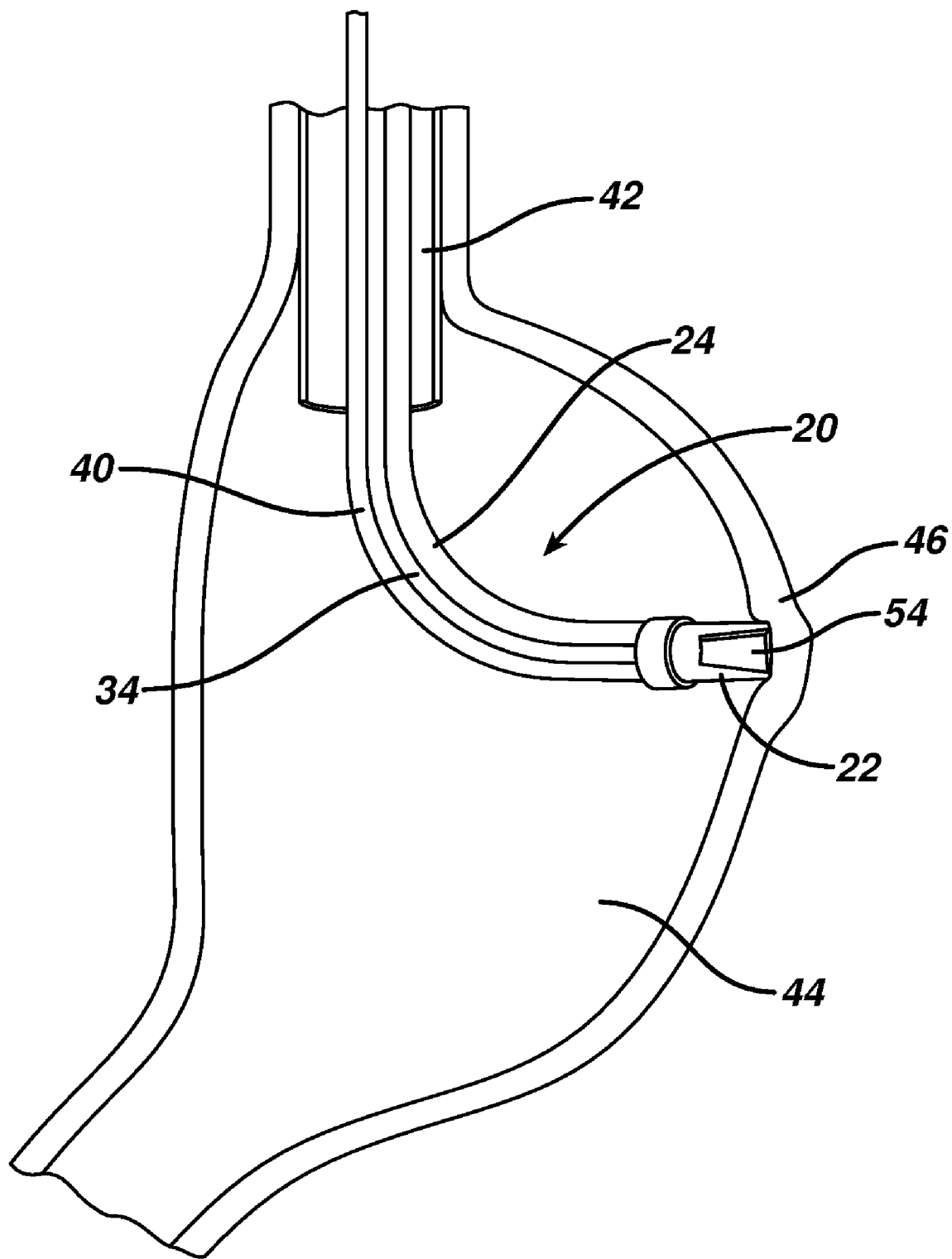
FIG. 2 is a diagrammatic view of the tissue plication device of FIG. 1, shown pushed into a tissue area in a gastric cavity.

To form a tissue plication, device 20 is inserted transorally through an esophageal overtube 42 and into a gastric cavity 44, as shown in FIG. 2. Folding member 22 is inserted through the esophagus and into the gastric cavity in an initial, closed position. This closed position allows for easier transfer into the gastric cavity. Following insertion, endoscope 24 is used to visualize the interior of cavity 44 (with a visualization device common to most endoscopes) and select the appropriate location for placement of a fold. After the location is determined, the distal tip of folding member 22 is pushed into the tissue wall 46 at the selected location, as shown in FIG. 2. Vacuum is then applied through vacuum line 34 to draw adjacent tissue into device 20. As vacuum is applied, the control assembly rotates folding member 22 into an open, tissue receiving position.

Figure 3A:
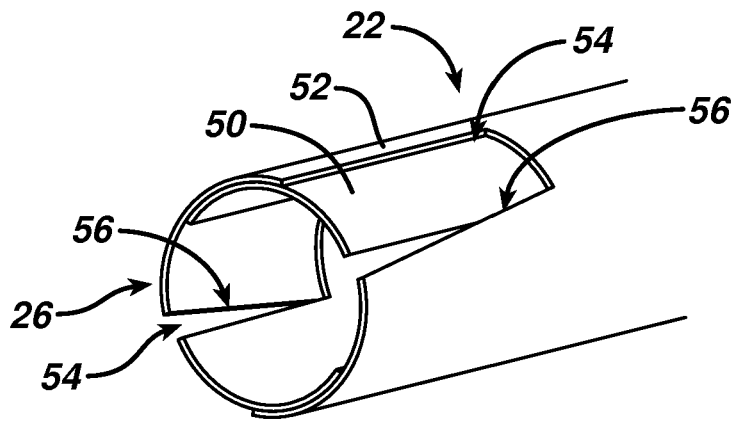
FIG. 3A is a more detailed, perspective view of the distal end of the tissue plicating device of FIG. 1, showing the tip of the device in an initial, closed position.
Figure 3B:
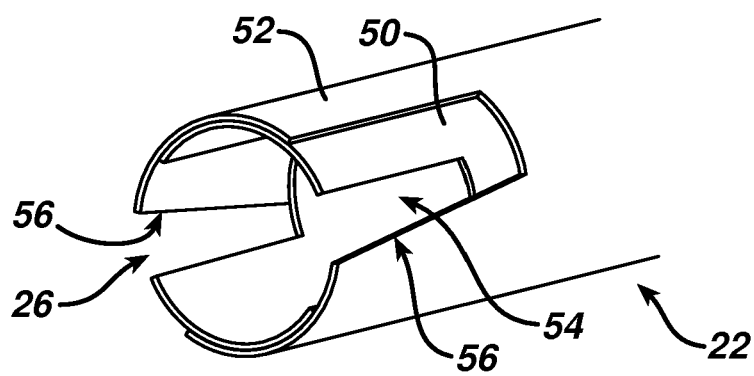
FIG. 3B is a more detailed, perspective view of the distal end of the tissue plicating device of FIG. 1, showing the tip of the device in a partially open position.
Figure 3C:
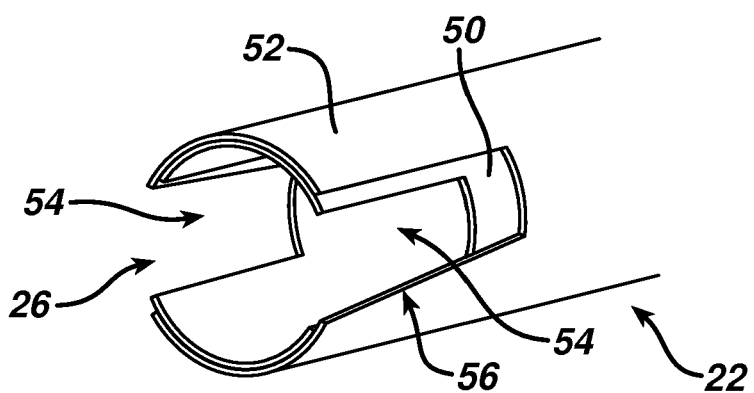
FIG. 3C is a more detailed, perspective view of the distal end of the tissue plicating device of FIG. 1, showing the tip of the device in a fully open, operative position.

FIGS. 3A-3C illustrate the distal end of folding member 22 in greater detail as the member is rotated from a closed to an open position. As shown in the FIGS., folding member 22 comprises a pair of concentric cylinders 50 (inner cylinder), 52 (outer cylinder) each having an open distal end 26. Lateral slots or apertures 54 extend from open end 26 into opposing sides of each of the cylinders 50, 52. One edge of each of the slots 54 is angled slightly inwardly, as indicated at 56, in order to guide tissue into the slots. In an initial position, shown in FIG. 3A, cylinders 50, 52 are positioned with the lateral slots 54 of the cylinders offset, thereby substantially closing the sides of the member. To form a tissue fold, one of the cylinders 50, 52 is rotated relative to the other cylinder to open lateral slots 54, as shown in FIG. 3B. As the cylinder is rotated to gradually open folding member 22, vacuum is applied to the tissue wall through distal opening 26 to pull the tissue into slots 54. After folding member 22 is fully opened, as shown in FIG. 3C, tissue fills slots 54 as the upper and lower layers of the tissue are folded together in a serosa to serosa configuration.

Figure 4:
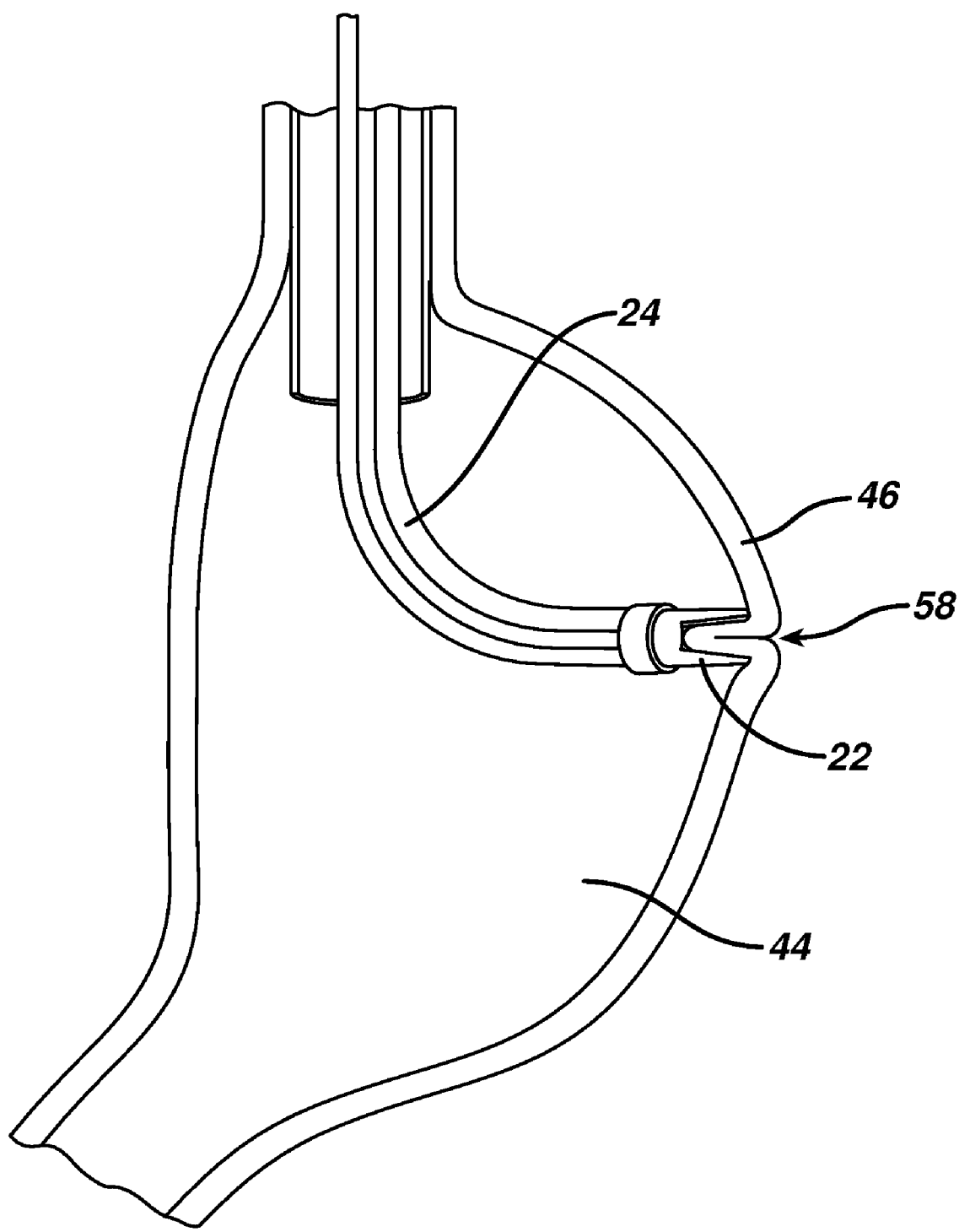
FIG. 4 is a diagrammatic view of the tissue plication device of FIG. 1, showing the device creating a fold in an area of tissue.

FIG. 4 illustrates device 20 with tissue wall 46 folded into a fully open folding member 22 to form a plication 58. After plication 58 is formed, a tissue fastening mechanism such as, for example, a stapler (not shown), is passed through the working channel of endoscope 24 to secure the plication. Alternatively, the end effector could be detached from the endoscope after the plication is made to secure the tissue together. This could be accomplished by any number of means known to those skilled in the art, such as placing matching detents on the cylinders which latch when the end effector is in its closed position.

After plication 58 is secured, the fastening mechanism is withdrawn, and the vacuum through line 34 turned off, to release the plication from folding member 22. Following release of the plication, cylinders 50, 52 are rotated to close folding member 22. Endoscope 24 and folding member 22 may then be moved to another location within the gastric cavity to form an additional plication. Once in the new location, vacuum is again applied to folding member 22 as the member is rotated open, to draw tissue into a fold within lateral slots 54. After folding, the tissue is again secured, the vacuum turned off, and folding member 22 rotated to a closed position. This procedure for forming a tissue plication may be repeated at multiple locations within the gastric cavity until the desired number of plications have been completed. In a typical bariatric procedure, it is anticipated that 5 or 6 plications would be formed within the gastric cavity to produce approximately a 50% volume reduction. A lesser or greater number of plications may be formed, however, depending upon the particular needs of the patient.

Figure 5:
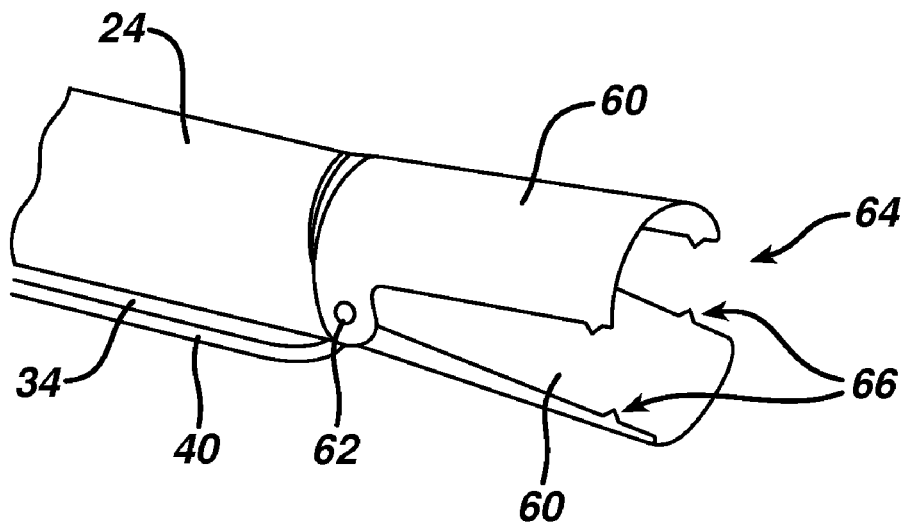
FIG. 5 is a perspective view of a second embodiment for the folding member of the tissue plicating device.
Figure 6:
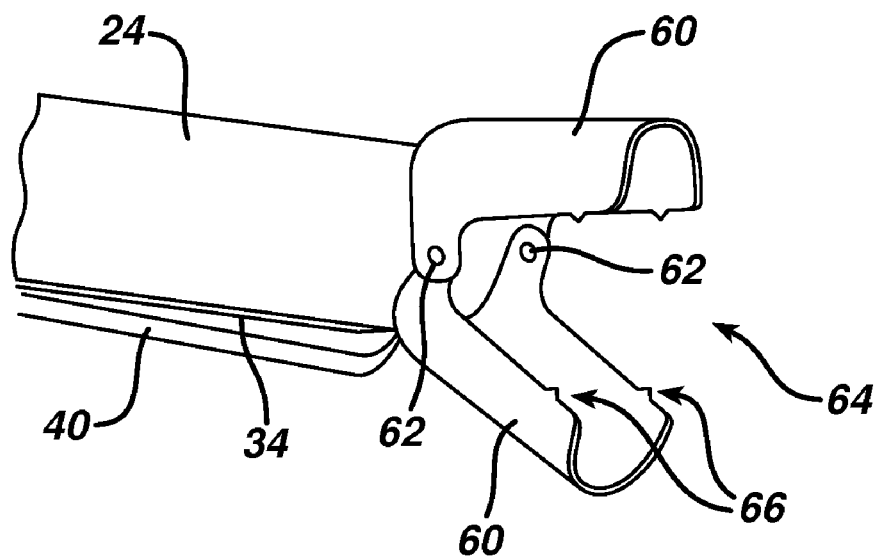
FIG. 6 is an additional perspective view of the folding member embodiment of FIG. 5, showing the folding member jaws in a fully open position.

FIGS. 5 and 6 illustrate an alternative embodiment for the folding member of the present invention. In this alternative embodiment, the tissue folding member comprises a pair of semi-circular reciprocating jaws 60 connected at the distal end of endoscope 24 by connecting member 30. Jaws 60 are attached together by pivot pins 62 to open and close relative to a distal opening 64. Each of jaws 60 is operated through control connection 40 to pivot outwardly relative to the axial centerline of the folding member. Vacuum is applied to the interior area between jaws 60 by vacuum line 34. Jaws 60 are initially in a closed position during transoral insertion into the gastric cavity. Once in the cavity, the distal edges of jaws 60 are pushed into the tissue wall at the desired plication location, in a manner similar to that described above with respect to the first folding member embodiment. Once jaws 60 are lodged in the tissue wall, the vacuum source is turned on, and the jaws are slowly opened to fold the tissue wall into the opening between the jaws. A pair of teeth 66 may be located adjacent the outer edge of each jaw 60 for grasping and holding the folding tissue in the jaws until the plication is secured and released. After jaws 60 are fully opened, as shown in FIG. 6, a tissue securing device may be passed through the working channel of endoscope 24 to secure the fold.

Figure 7:
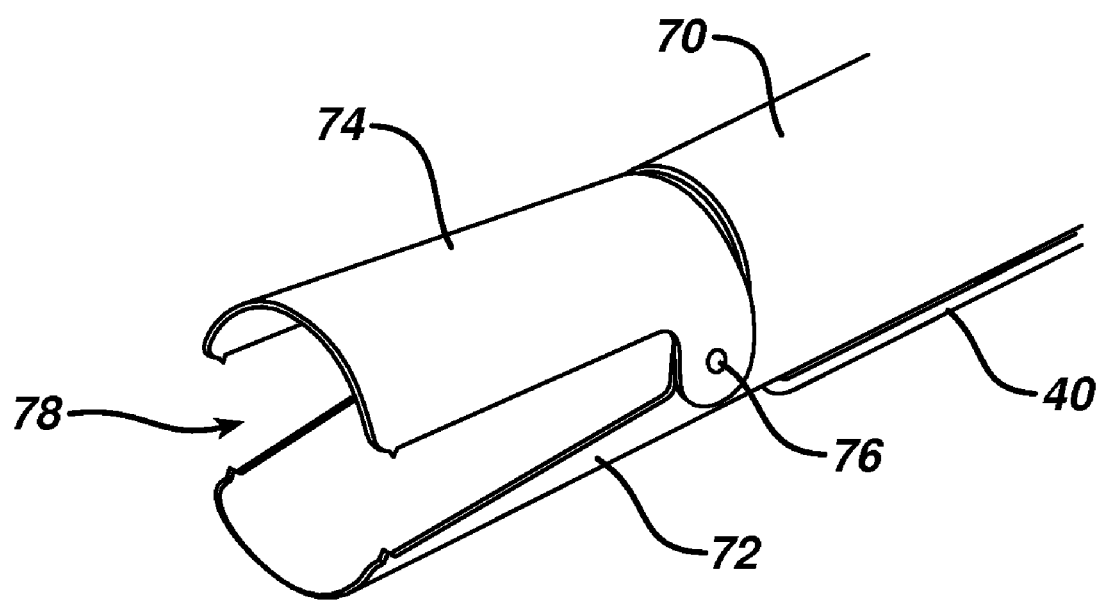
FIG. 7 is a perspective view of a third embodiment for the folding member of the present invention.

In an alternative embodiment to that shown in FIGS. 5 and 6, the tissue folding member may comprise a set of tissue grasping jaws in which one jaw rotates relative to a fixed second jaw. In this embodiment, shown in FIG. 7, the folding member comprises a cylinder 70 with the upper portion cutaway to form a fixed lower jaw 72. Lower jaw 72 extends axially from cylinder 70 as a semi-circular distal projection. A mating, semi-circular upper jaw 74 is attached to the folding member by pivot pins 76. Upper jaw 74 extends in a parallel fashion to lower jaw extension 72. To form a tissue fold, vacuum is applied through the interior of cylinder 70 to draw the tissue wall proximally into an opening 78 between jaws 72, 74. As tissue is pulled between the jaws, upper jaw 74 is pivoted away from lower jaw 72, via control connection 40, to increase the size of the tissue opening and allow the tissue wall to fold into the opening. After upper jaw 74 is pivoted to a fully open position, the folded tissue between the jaws is secured by a fastening device passed through endoscope 24. Vacuum is then turned off, and the secured plication released from the folding member.

Figure 8:
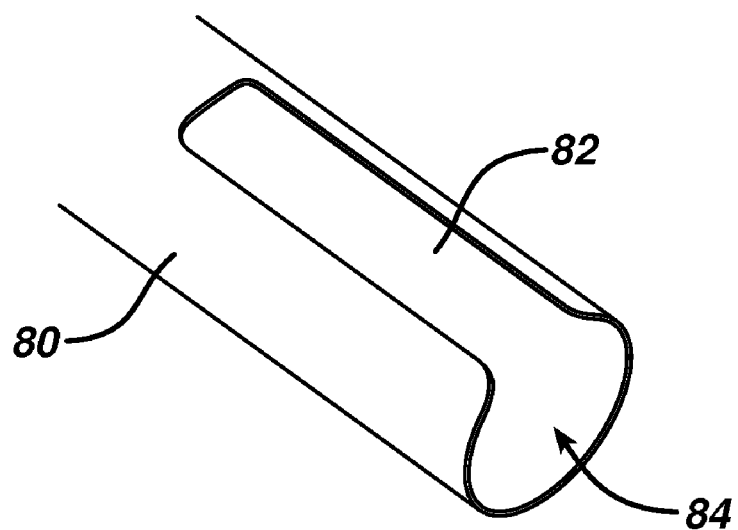
FIG. 8 is a perspective view of a fourth embodiment for the folding member.

FIG. 8 illustrates another alternative embodiment for the folding member of the present invention. In this embodiment, tissue folding is accomplished through a cylindrical end piece 80 attached by connecting member 30 at the distal tip of endoscope 24. End piece 80 includes a side slot 82 that extends proximally from an open distal end 84. Vacuum is applied through the interior of end piece 80 to draw tissue into open end 84 and up into slot 82. As the tissue is pulled into slot 82, the walls of the tissue are folded together. After the tissue has been fully drawn up into slot 82, a securing device may be passed through endoscope 24 to affix the tissue layers together. Following tissue securement, the vacuum through line 34 is turned off to release the tissue plication from distal end 84.

Figure 9:
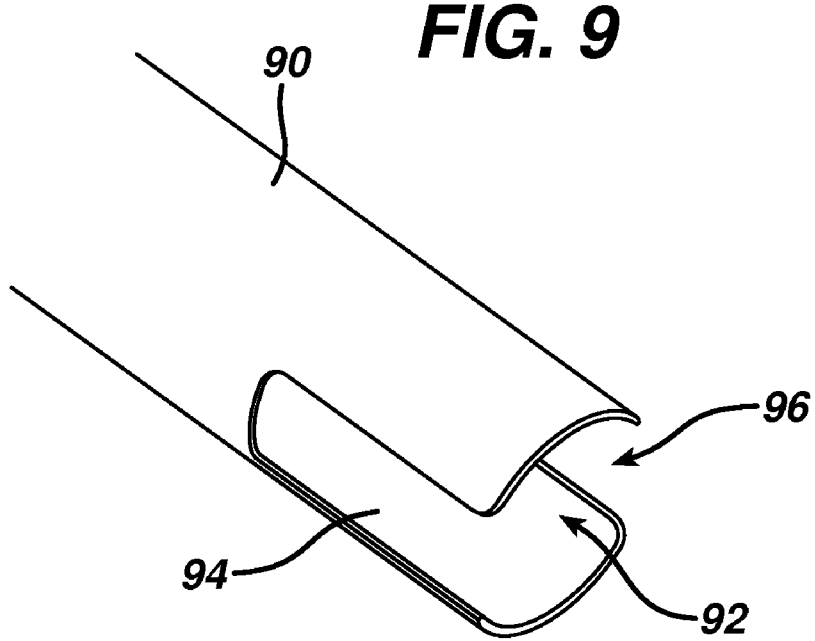
FIG. 9 is a perspective view of a fifth embodiment for the folding member.

FIG. 9 shows yet another embodiment for a tissue folding member of the present invention, in which the member comprises a cylinder 90 having an open distal end 92 and a pair of side slot openings 94, 96. In this embodiment, vacuum is applied through cylinder 90 and open distal end 92 to draw tissue into the device. As tissue is pulled into the device, the tissue expands up into side slots 94, 96. As tissue is drawn into side slots 94, 96 a fold is formed therein. After the tissue as been fully drawn up into slots 94, 96, a securing device may be passed through endoscope 24 to affix the tissue layers together. Following tissue securement, the vacuum through line 34 is turned off, and the device retracted away from the cavity wall in order to release the tissue plication from distal end 92. The folding member embodiments shown in FIGS. 8 and 9 both comprise a fixed cylindrical body for drawing tissue into the device. Accordingly, these embodiments eliminate the need to extend a control connection 40 to the distal end of the device in order to operate the folding member.

Figure 10A:
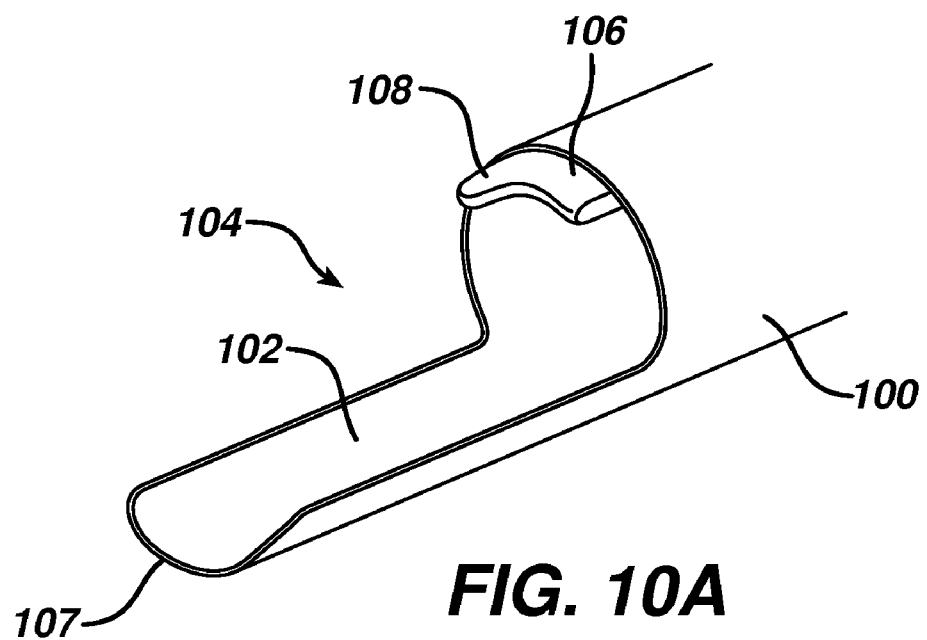
FIG. 10A is a perspective view of a sixth embodiment for the folding member showing a retractable jaw of the member in a first, retracted position.
Figure 10B:
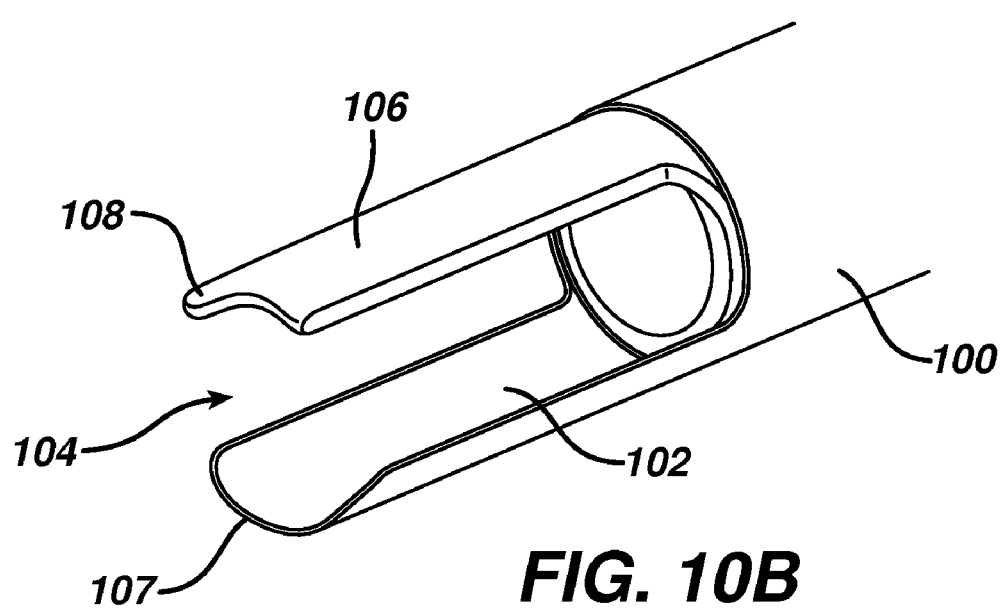
FIG. 10B is an additional perspective of the sixth folding member embodiment, showing the retractable jaw in a forward projected position.

FIGS. 10A and 10B illustrate an additional embodiment for a tissue folding member of the present invention. In this embodiment, the folding member comprises a cylindrical piece 100 having a first, fixed jaw 102 projecting from an open end 104. A second, retractable jaw 106 extends into open end 104 on a side opposite fixed jaw 102. To form a tissue fold in this embodiment, the distal tip 107 of the folding member is pushed into the gastric tissue wall at a desired plication location. Second jaw 106 is initially in a retracted position, shown in FIG. 10A, when the folding member is positioned against the tissue wall. Once tissue contact is made at the desired location, vacuum from line 34 is applied through the interior of cylinder 100 to pull tissue onto first jaw 102. After the tissue wall is engaged with first jaw 102, second jaw 106 is moved distally, substantially parallel to first jaw 102, to pull the tissue outward and fold the tissue over the first jaw. The tip of second jaw 106 is radii smooth, as indicated by reference numeral 108, to facilitate the second jaw sliding over the tissue. After second jaw 106 is fully extended, as shown in FIG. 10B, a fastening mechanism is passed through the interior of cylinder 100 to fasten the plication. After fastening, the vacuum through cylinder 100 is turned off, and jaw 106 retracted back into cylinder 100. The folding member may then be moved to a new tissue location to form additional plications, or removed from the patient.

Figure 11:
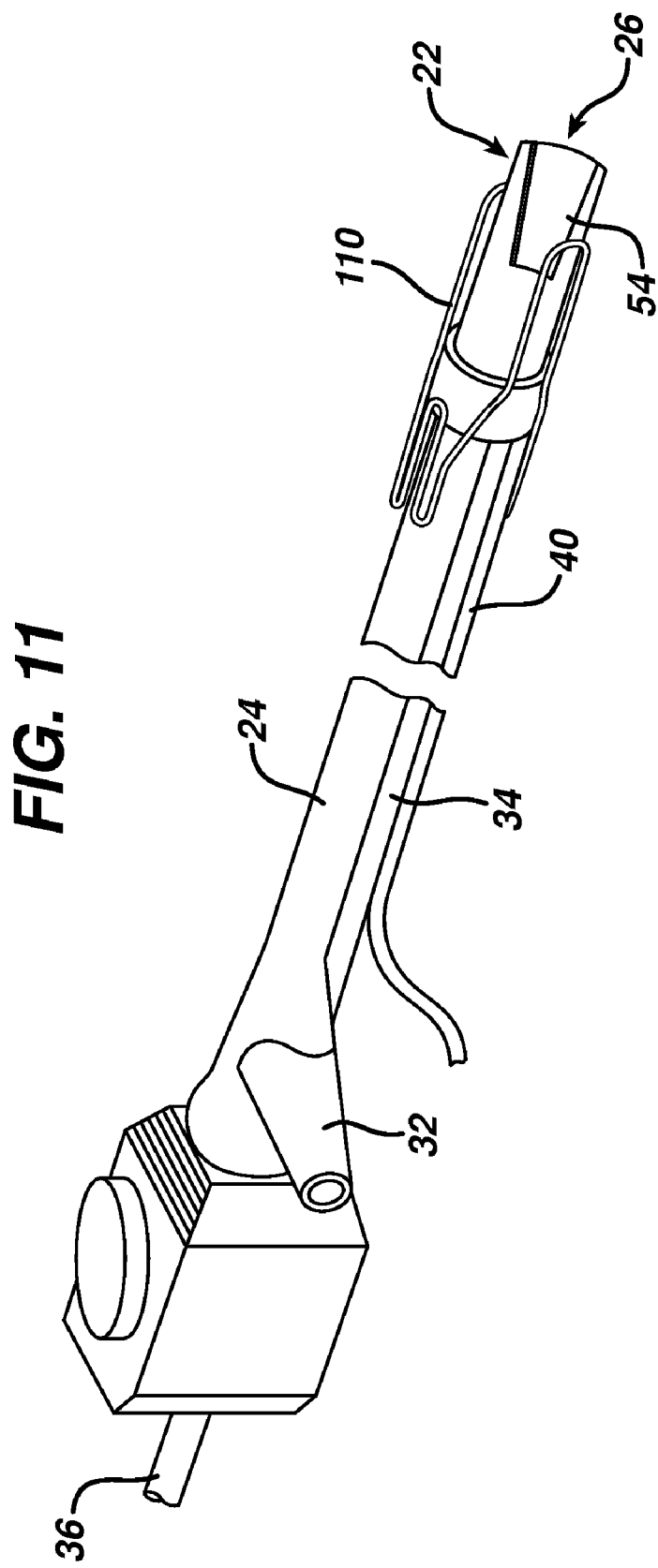
FIG. 11 shows an alternative embodiment for the tissue plicating device of the present invention, in which the device further comprises a tissue fastening member.

In alternative embodiments for gastric plicating device 20, the device further comprises a fastening means for securing the tissue plication subsequent to tissue folding. Use of a fastening means on device 20 eliminates the need to pass a separate tissue fastening mechanism through endoscope 24 after folding in order to secure the plication. In the embodiment shown in FIG. 11, a fastening member 110 is disposed adjacent the distal end of the device for transfer from the device to a plication after folding. Fastening member 110 is held sufficiently secure on device 20 to be passed along with endoscope 24 and folding member 22 into the gastric cavity, yet is removable through control connection 40 at the end of a tissue folding procedure to secure a plication. In the embodiment shown in FIG. 11, the fastening member is a wire clip 110 which is retained on connecting member 30 just proximal of the tissue folding slots 54 in folding member 22. Wire clip 110 is contoured to surround the perimeter of connecting member 30 and folding member 22 and be retained thereon during device insertion.

Figure 12A:
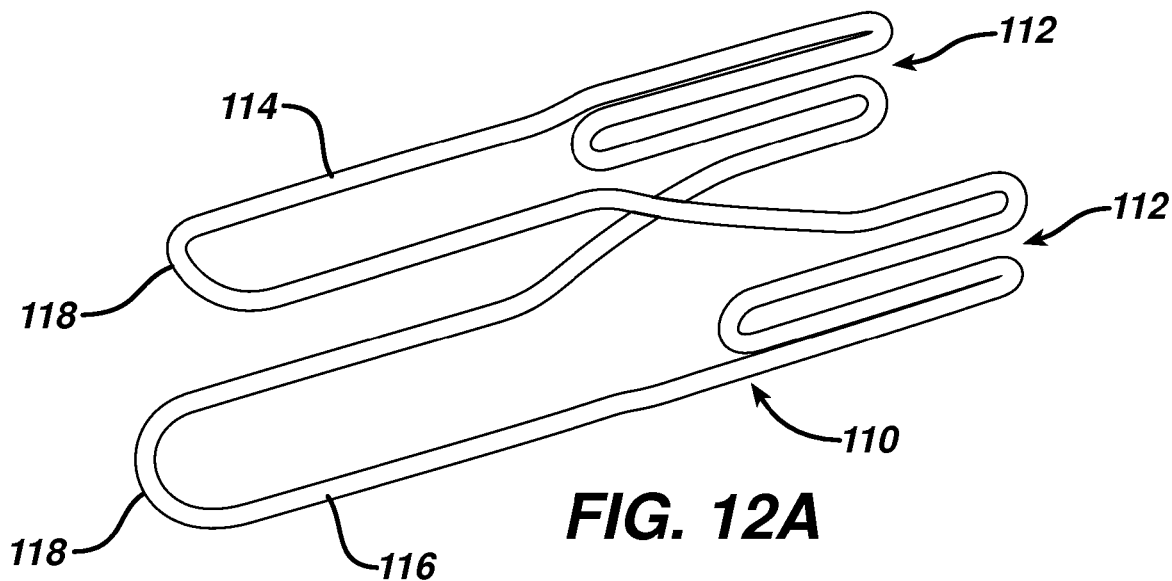
FIG. 12A is a more detailed, perspective view of the fastener embodiment shown in FIG. 11.
Figure 12B:
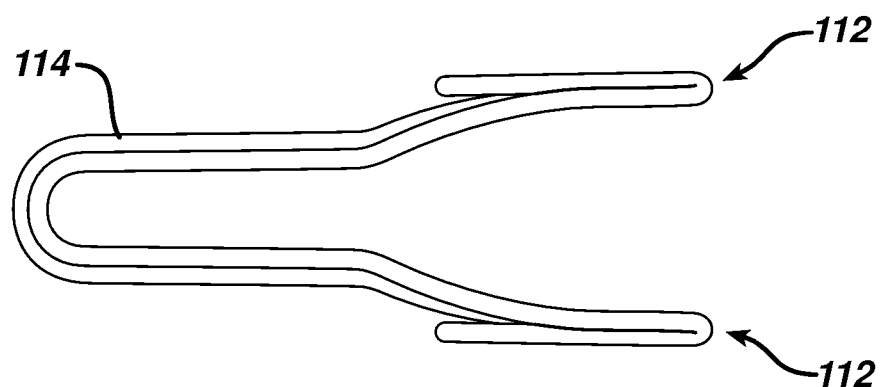
FIG. 12B is a top view of the fastener embodiment shown in FIG. 11.
Figure 12C:
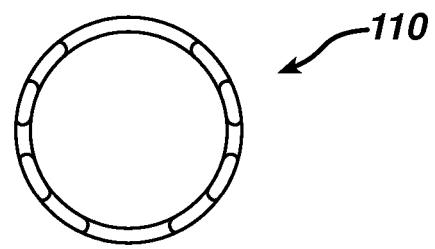
FIG. 12C is an end view of the fastener embodiment shown in FIG. 11.

As shown in greater detail in FIGS. 12A-12C, wire clip 110 comprises a continuous length of thin gauge wire. The proximal end of clip 110 is shaped on opposing sides in a spring form, indicated by reference numeral 112, to assist in generating sufficient force to clamp onto the folded tissue. From spring form 112, the wire is shaped into a pair of telescoping jaws 114, 116, as shown in FIG. 12B. Jaws 114, 116 extend distally from spring forms 112 in a parallel fashion to slide along the upper and lower surfaces of a tissue fold. The distal tips 118 of jaws 114, 116 may flare outwardly from the axial centerline of clip 110 to facilitate lead-in of the lip onto a tissue fold. As shown in FIG. 12C, clip 110 has a substantially circular cross-section to conform to the shape of connecting member 30 to aid in retaining the clip on the folding member during the transoral insertion of device 20. After tissue folding, control connection 40 engages clip 110 to release the clip from folding member 22, and slide the clip onto the tissue fold.

Figure 13:
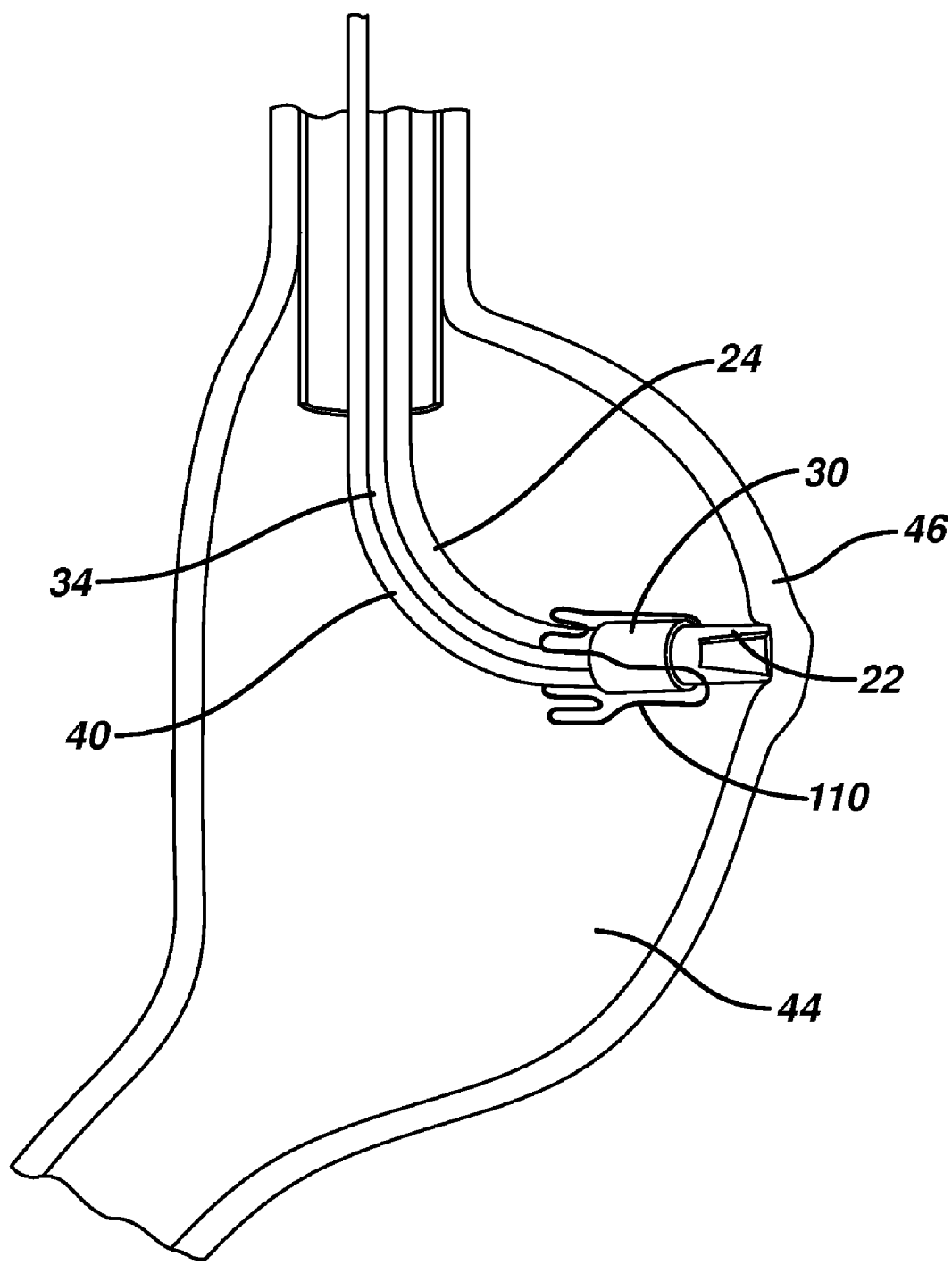
FIG. 13 is a diagrammatic view of the tissue plication device of FIG. 11, showing the device pushed into a tissue wall within a gastric cavity.
Figure 14:
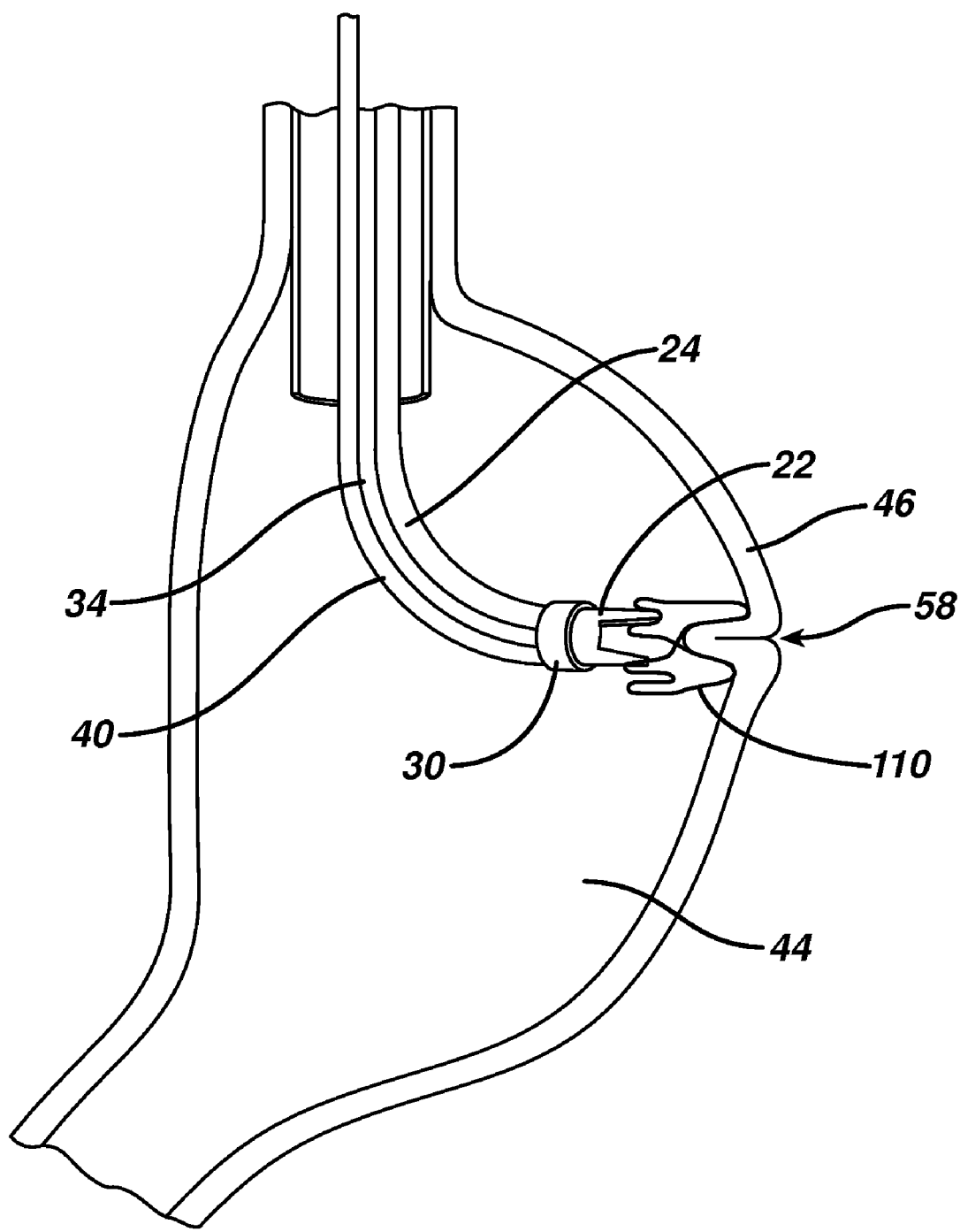
FIG. 14 is a diagrammatic view of the tissue plication device of FIG. 11, showing the device placing a fastener on a tissue fold.
Figure 15:
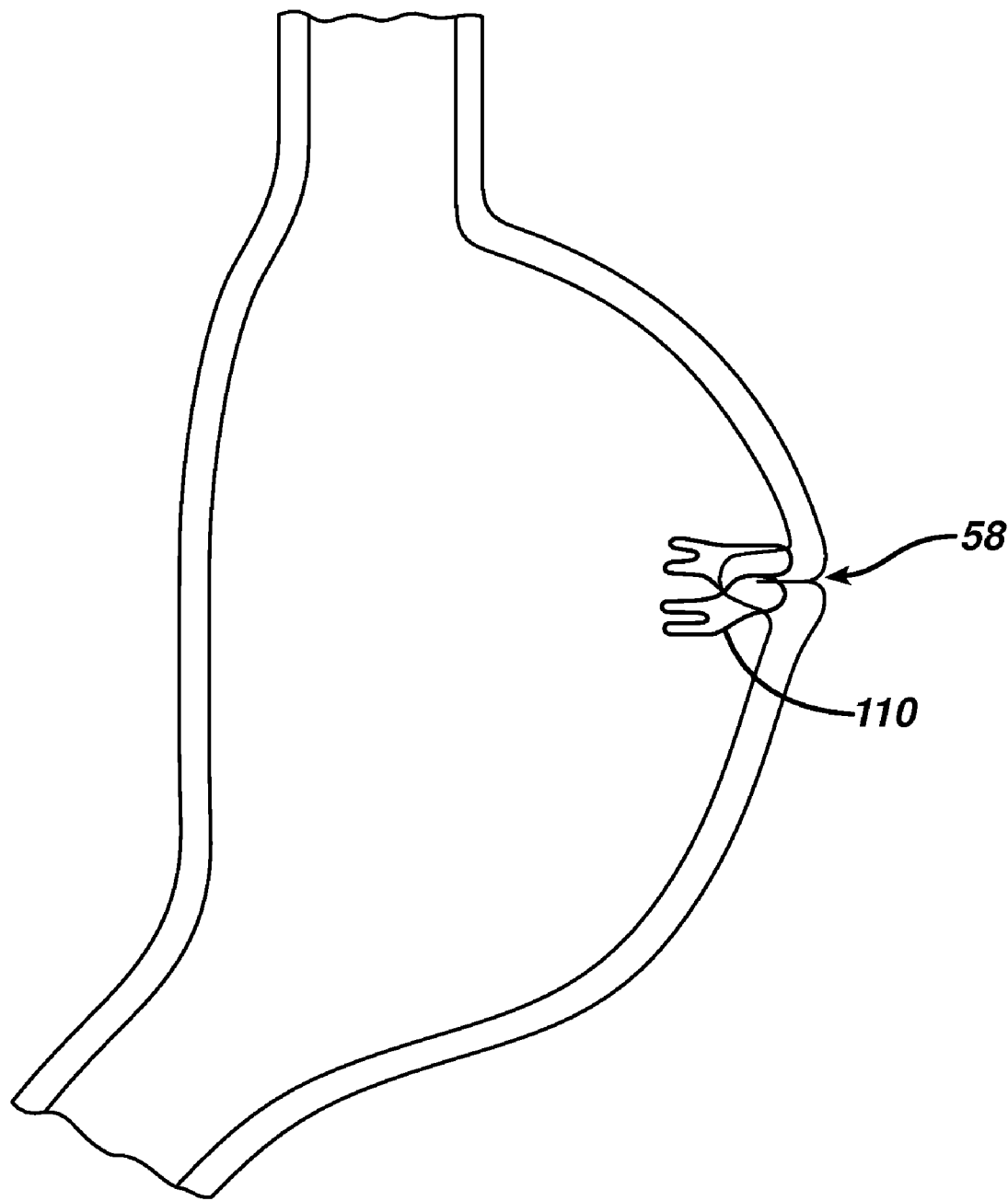
FIG. 15 is a diagrammatic view similar to FIG. 14, showing the gastric cavity subsequent to folding and placement of a fastening member.

FIG. 13 illustrates device 20 with wire clip 110 disposed thereon engaging a gastric tissue wall prior to folding. As shown in FIG. 13, clip 110 is carried on connecting member 30 as device 20 is inserted into gastric cavity 44 and pushed into tissue wall 46 at a desired plication location. FIG. 14 similarly illustrates gastric cavity 44 as vacuum is applied through folding member 22 to draw tissue wall 46 into a fold. As the tissue fold is formed, jaws 114, 116 of clip 110 expand and move over folding member 22 to initially engage the tissue fold. After upper and lower layers of tissue wall 46 are folded together within slots 54, clip 110 is released from folding member 22 so that jaws 114, 116 clamp down on plication 58. Jaws 114, 116 clamp onto plication 58 due to the energy stored in spring forms 112. After clip 110 engages plication 58, the vacuum to folding member 22 is turned off, and the remainder of device 20 moved away from the plication location, leaving the fastened plication as shown in FIG. 15.

Figure 16A:
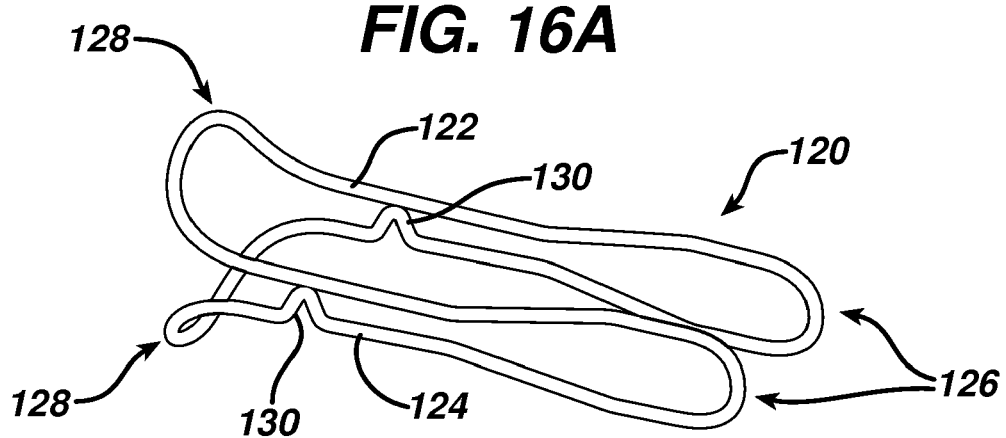
FIG. 16A is a perspective view of an alternative embodiment for a tissue plication fastener.
Figure 16B:
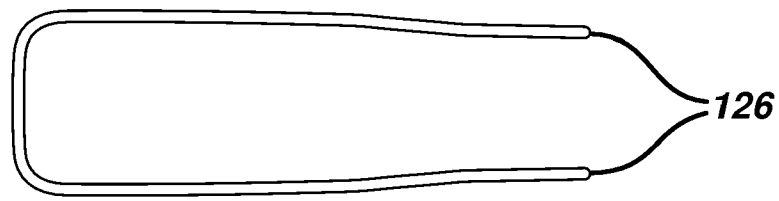
FIG. 16B is a top view of the alternative fastener shown in FIG. 16A.
Figure 16C:
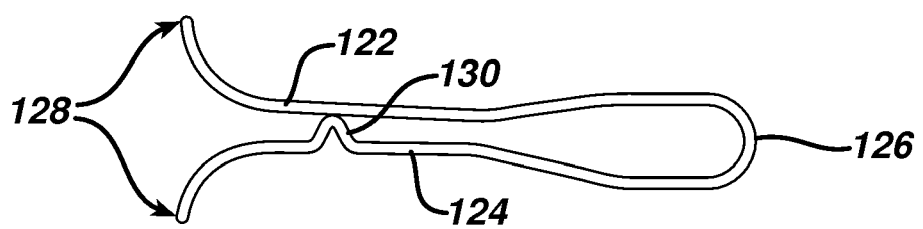
FIG. 16C is a side view of the alternative fastener shown in FIG. 16A.
Figure 16D:
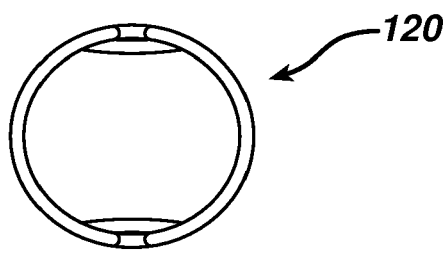
FIG. 16D is an end view of the alternative fastener shown in FIG. 16A.

FIGS. 16A-16D illustrate an alternative embodiment for a tissue fastener usable with folding member 22 of the invention. In this embodiment, the fastener comprises a continuous wire clip 120 formed into a pair of parallel extending jaws 122, 124 that engage a tissue fold. Jaws 122, 124 each comprise a pair of evenly spaced wire lengths that are bent at 180° angles at the proximal ends of the clip, as indicated by reference numeral 126. The distal ends of jaws 122, 124 flare outwardly, as indicated at 128, to enhance lead-in of the clip onto the tissue fold. Clip 120 also comprises one or more wire shapes for preventing slippage of the clip along the tissue fold. As shown in FIG. 16C, these wire shapes may comprise indentations or "teeth" 130 placed along the length of either of jaws 122 or 124. As shown in FIG. 16D, clip 120 has a substantially circular cross-section that follows the contour of connecting member 30 and folding member 22 to retain the clip on device 20 until released onto a tissue fold through control connection 40.

Figure 17:
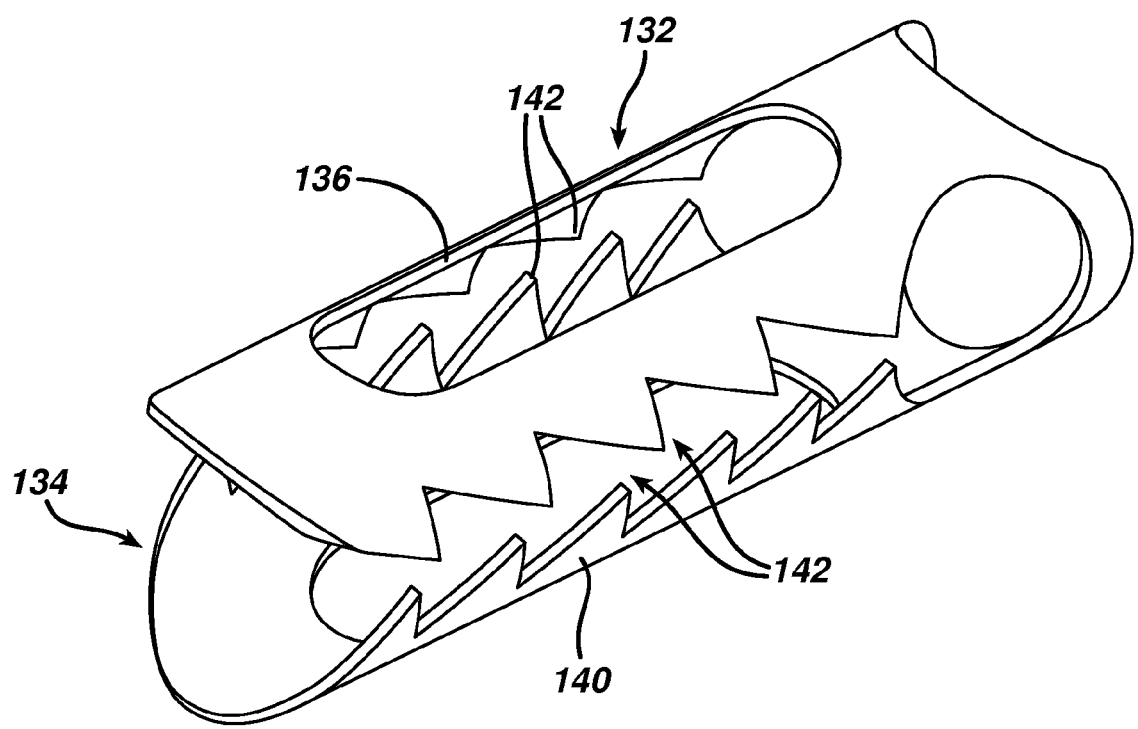
FIG. 17 is a perspective view of a third embodiment for a tissue fastener in accordance with the present invention.

FIG. 17 illustrates a third embodiment for a tissue fastener in accordance with the present invention. As shown in FIG. 17, in this embodiment the tissue fastener comprises a tubular-shaped clip 132. Clip 132 has an inner diameter that is sized to contour the outer perimeter of connecting member 30 to retain the clip thereon until released onto a fold. Clip 132 has an open distal end 134 for engaging a tissue fold. A pair of semi-circular jaws 136, 140 extends along the axial length of clip 132 for engaging a tissue fold as the clip is transferred onto the fold through control connection 40. Jaws 136, 140 each have a rounded distal end for facilitating transfer of clip 132 onto the tissue fold. A plurality of teeth, indicated by reference numeral 142, extend from the inwardly facing edges of jaws 136, 140 to grasp and hold tissue within the clip, thereby preventing the clip from dislodging from the tissue fold after fastening. Clip 132 can be manufactured from either a plastic or a metallic material. Clip 132 can also be made from absorbable material where it will dissolve away after three weeks and pass through the digestive tract safely. It could be made of laminate construction as small particles of absorbable material would pass and no large parts can come off all at once.

Figure 18A:
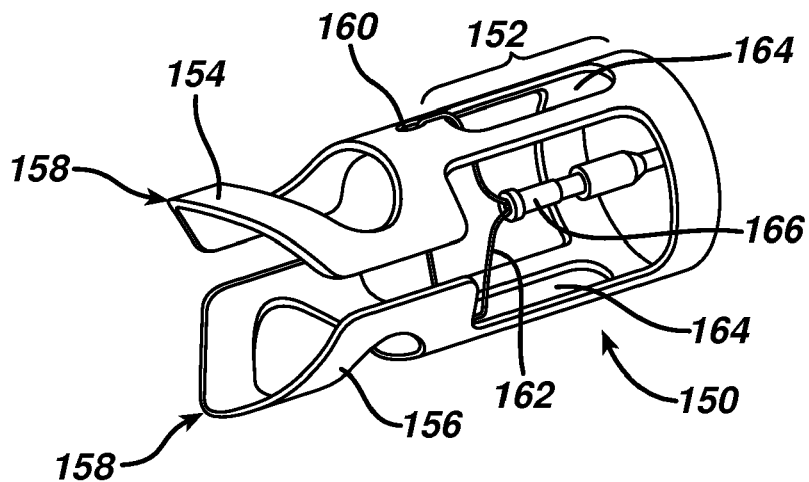
FIG. 18A is a perspective view of a fourth embodiment for a tissue fastening device.
Figure 18B:
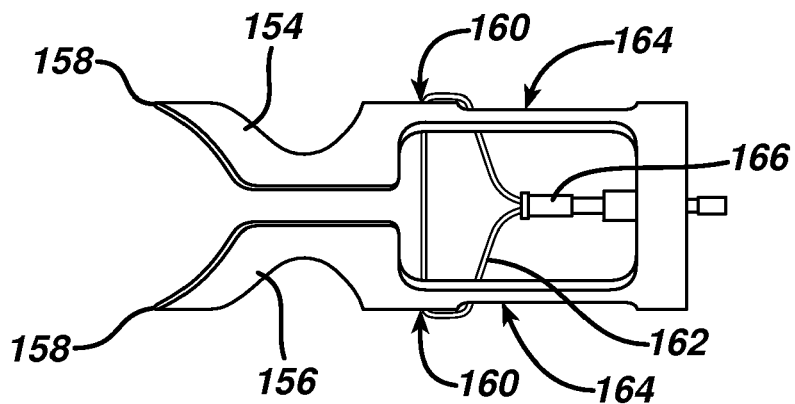
FIG. 18B is a side view of the tissue fastening device shown in FIG. 18A.
Figure 18C:
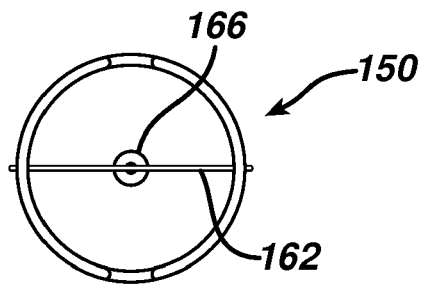
FIG. 18C is an end view of the tissue fastening device shown in FIG. 18A.

FIGS. 18A-18C illustrate another alternative embodiment for a tissue fastening member of the present invention. In this embodiment, a fastener 150 comprises a proximal frame area 152 having a cylindrical contour for fitting about the perimeter of connecting member 30. The distal end of fastener 150 comprises a pair of semicircular, tissue engaging jaws 154, 156. Jaws 154, 156 each have a tapered distal edge, as indicated at 158, to provide a lead-in for engaging a tissue fold. A pair of holes 160 are located in a midsection of fastener 150, between proximal frame area 152 and jaws 154, 156. Holes 160 extend perpendicular to the axial length of the fastener. A suture 162 passes through holes 160 and then proximally through openings 164 in frame area 152. After jaws 154, 156 engage a tissue fold, suture 162 is tightened through holes 160 and openings 164 to pull jaws 154, 156 inwardly towards the tissue fold. As jaws 154, 156 are pulled inwardly, the jaws deflect laterally along the upper and lower surfaces of the fold, clamping the fold between the jaws. A suture lock 166 is placed on suture 162 after tissue fastening, to prevent the suture from relaxing and releasing the tissue fold from jaws 154, 156.

Figure 19A:
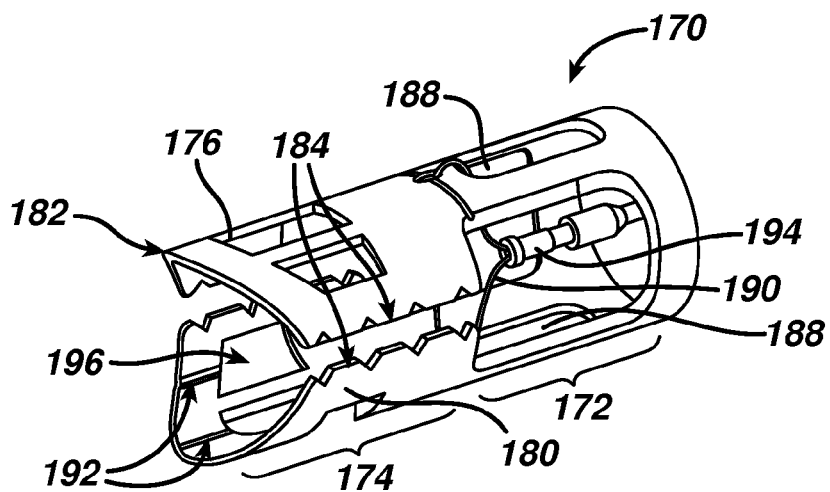
FIG. 19A is a perspective view of a fifth embodiment for a tissue fastening device.
Figure 19B:
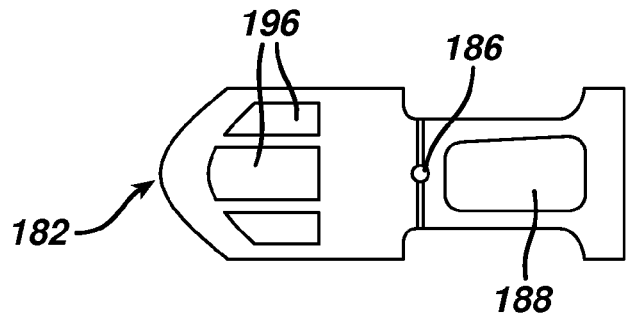
FIG. 19B is a top view of the tissue fastening device shown in FIG. 19A.
Figure 19C:
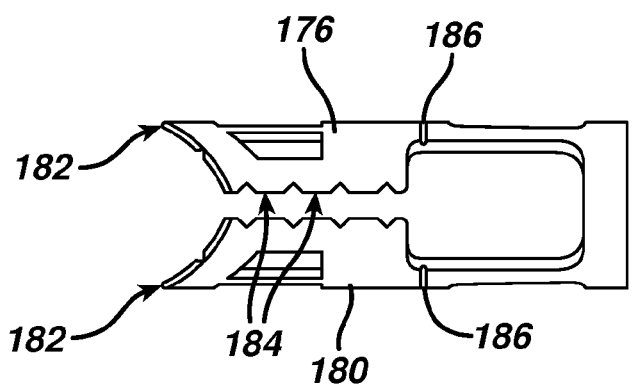
FIG. 19C is a side view of the tissue fastening device shown in FIG. 19A.

FIGS. 19A-19C illustrate yet another alternative embodiment for the fastening means of the present invention. In FIGS. 19A-19C, a fastener 170 is shown having a proximal frame area 172 and a distal clamping area 174. Proximal frame area 172 has a cylindrical cross-section for retaining fastener 170 about the perimeter of connecting member 30. Clamping area 174 comprises a pair of semicircular, tissue engaging jaws 176, 180. Jaws 176, 180 each have a tapered distal edge, as indicated at 182, for ease in engaging a tissue fold. Additionally, rows of tissue grasping teeth 184 extend along the inward facing edges of jaws 176, 180 to prevent the fastener from slipping along the tissue fold. A pair of holes 186 is located in a midsection of fastener 170, between frame area 172 and clamping area 174. Holes 186 extend perpendicular to the axial length of the fastener. In a manner similar to the embodiment shown in FIGS. 18A-18C, a suture 190 passes through holes 186 and openings 188 to clamp jaws 176, 180 inwardly onto a tissue fold. A plurality of notches, indicated by reference numeral 192, extend axially along the distal end of jaws 176, 180. Notches 192 allow jaws 176, 180 to flatten out along the surface of the tissue fold when tightened by suture 190. Notches 192 also facilitate the application of an even clamping force to the fold. A suture lock 194 is placed on suture 190 to prevent the suture from relaxing and releasing the tissue fold from jaws 176, 180. An additional plurality of openings 196 extend through clamping area 174 to enable fastener 170 to be stitched closed from the inside of the cavity, in order to further secure the tissue fold.

Figure 20A:
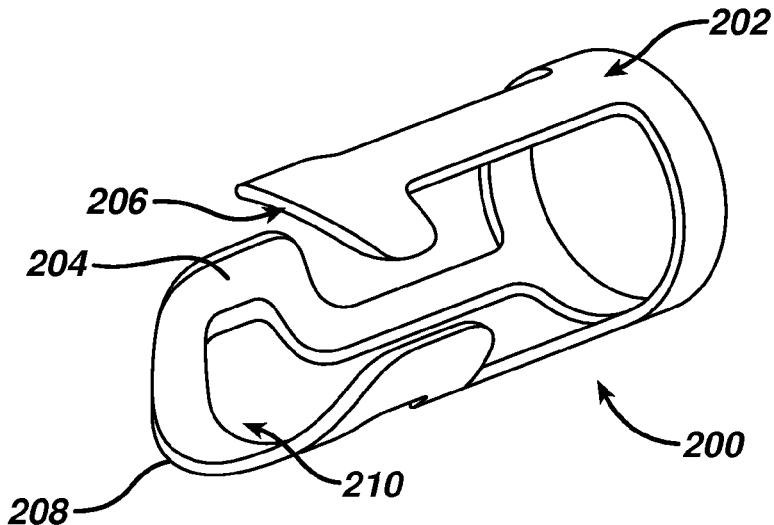
FIG. 20A is a perspective view of a sixth embodiment for a tissue fastening device.
Figure 20B:
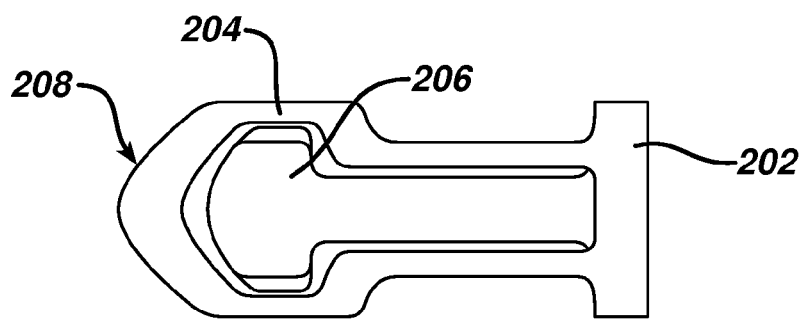
FIG. 20B is a top view of the tissue fastening device shown in FIG. 20A.
Figure 20C:
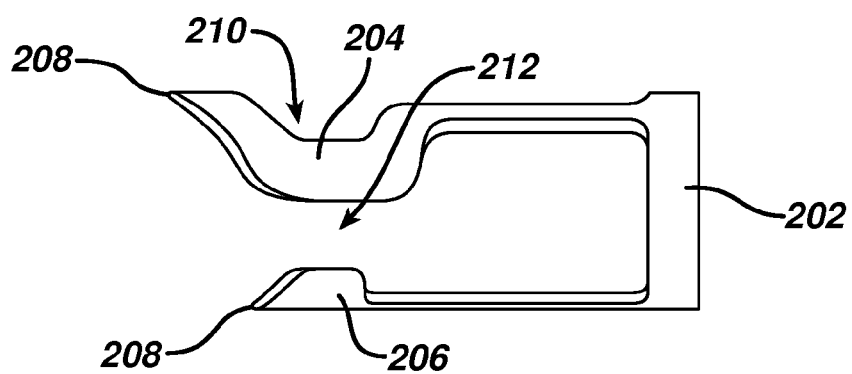
FIG. 20C is a side view of the tissue fastening device shown in FIG. 20A.

FIGS. 20A-20C illustrate another alternative embodiment for the tissue fastening means of the present invention. In this embodiment, a fastener 200 comprises a rig 202 and a pair of telescoping jaws 204, 206 extending distally from the ring. The distal edges of jaws 204, 206 are tapered, as indicated at 208, to provide a lead-in edge for fastener 200 to roll over a tissue fold. The first jaw 204 comprises a cutout 210 that mirrors the outer profile of the second jaw 206 to enable the jaws to interdigitate when the jaws are clamped together on a tissue fold. Jaws 204, 206 are preloaded towards an axial centerline 212 of the fastener to compress and hold the folded tissue as the fastener is drawn over the fold.

Figure 21:
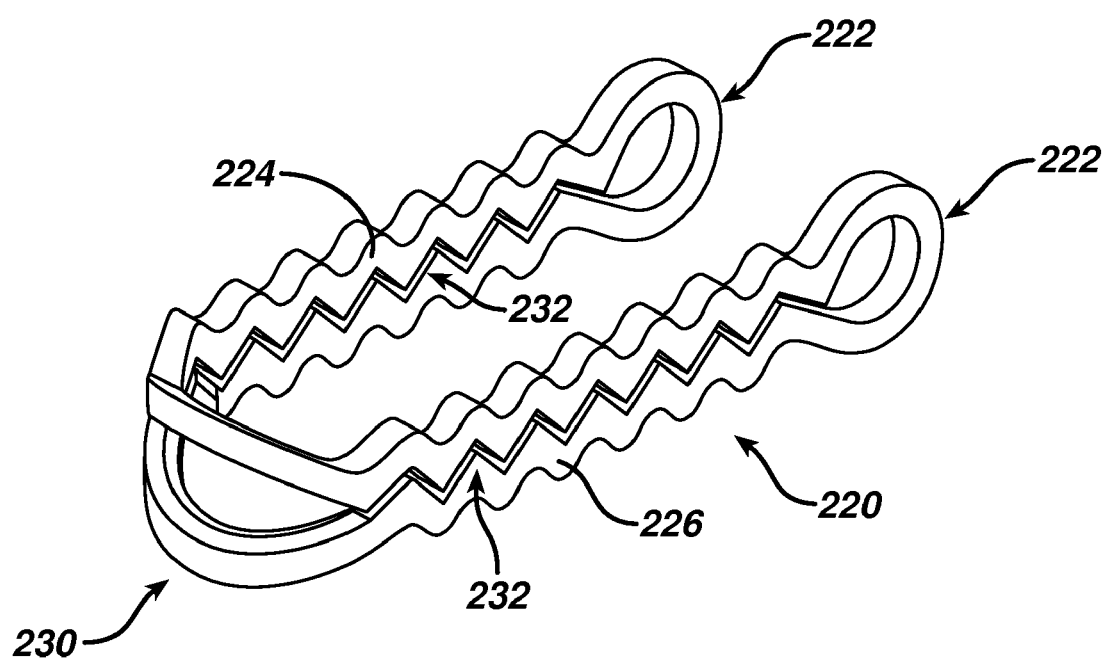
FIG. 21 is a perspective view of a seventh embodiment for a tissue fastening device of the present invention.

FIG. 21 illustrates yet another clip 220 for fastening a tissue fold. Clip 220 comprises a proximal spring end 222. A pair of jaws 224, 226 project forward from spring end 222 to a rounded distal end 230. Distal end 230 is rounded to facilitate placement of clip 220 on a tissue fold. Spring end 222 serves to clamp jaws 224, 226 on a tissue fold and inhibit the clip from slipping along the fold. To further prevent clip 220 from releasing from a tissue fold, a plurality of serrated teeth 232 extend substantially along the length of jaws 224, 226. Teeth 232 may be angled proximally to prevent clip 220 from being removed from the tissue fold. Alternatively, teeth 232 may be angled distally to enable clip 220 to be removed from a fold provided tissue has not grown over the clip. In the clip depicted in FIG. 21, teeth 232 are placed at a 45 degree angle to hold tissue securely, yet enable subsequent removal of the clip should such removal be required.

Figure 22:
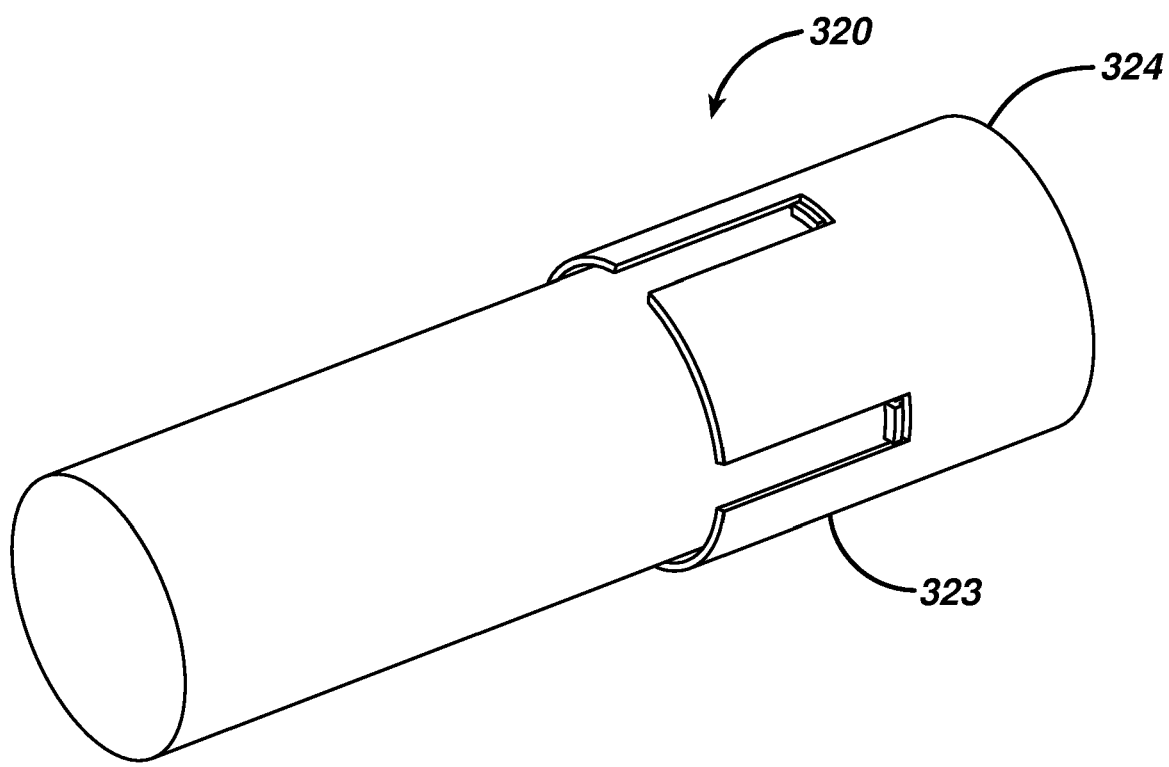
FIG. 22 is a perspective view of an additional embodiment for the tissue plicating implant device of the present invention.
Figure 23:
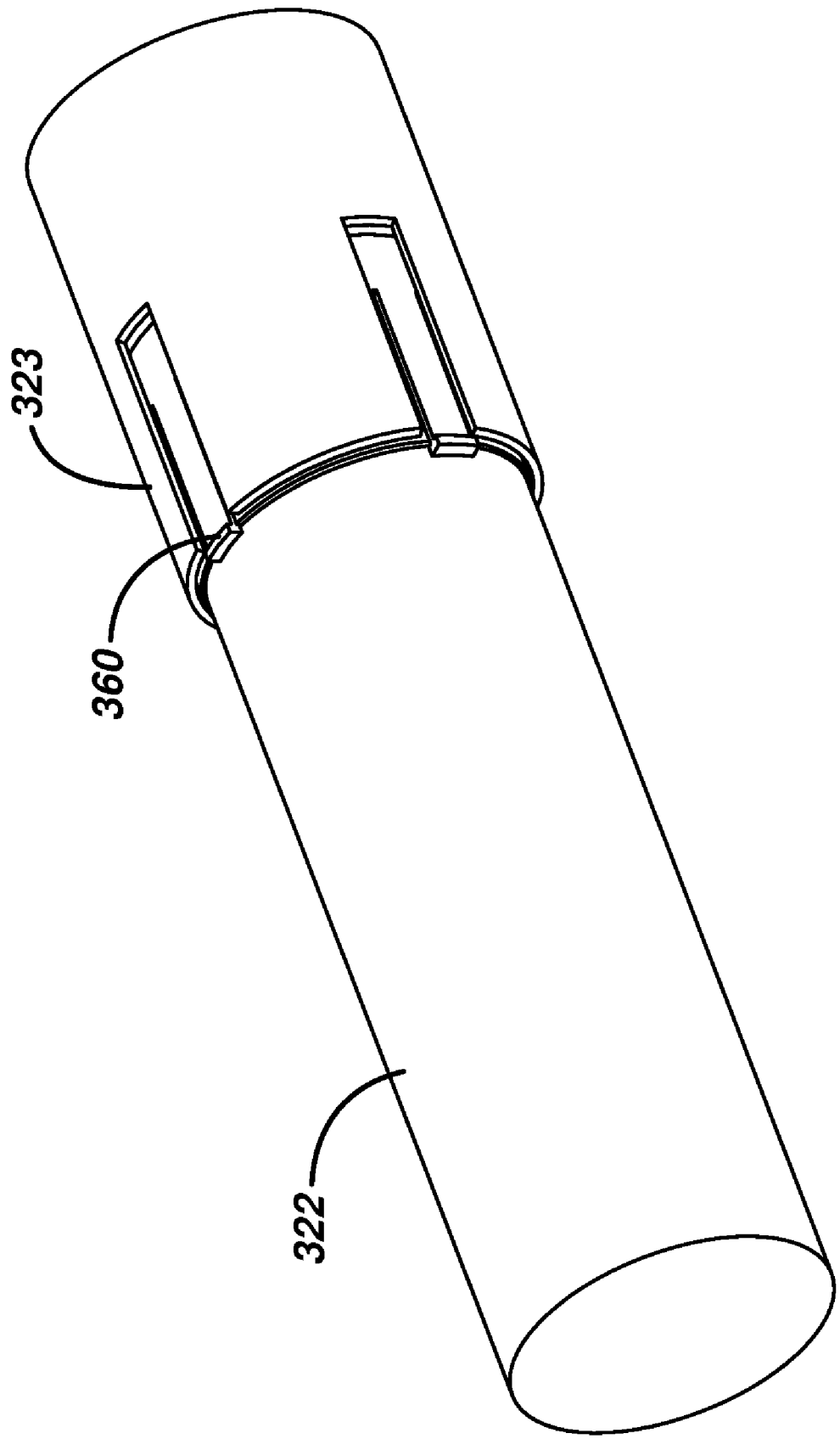
FIG. 23 is a view similar to that shown in FIG. 22 but showing the device in its partially deployed position.

Yet another embodiment of the present invention is described in FIGS. 22-24 which shows tissue plicating device 320. Device 320 is similar to device 20 described above, however the end effector 323 of device 320 is detachable from the distal end 232 of endoscope 324. After the tissue is acquired and pinched within end effector 323 (such as described in FIGS. 25 below), a push rod within the endoscope (not shown) pushes on collar 350, moving the end effector 323 distally so as to expose legs 360. Legs 360 are biased outwardly such that as they move distally the remove their grip on the end effector 323, thereby releasing end effector 323 from attachment with the scope 324.

Figure 25A:
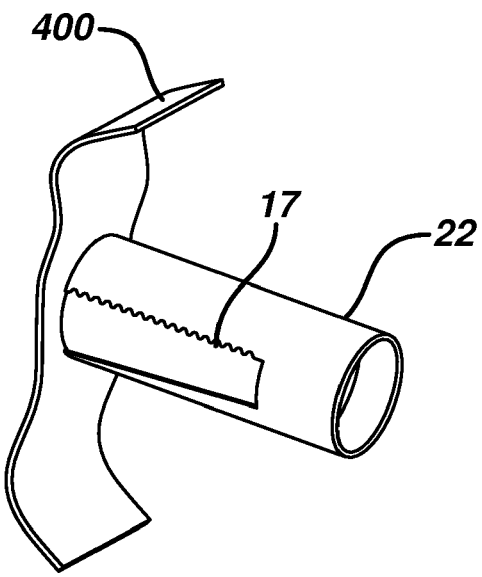
FIG. 25A-25D are simplified perspective views of the device shown in FIG. 1 actually acquiring tissue and forming a plication.
Figure 25B:
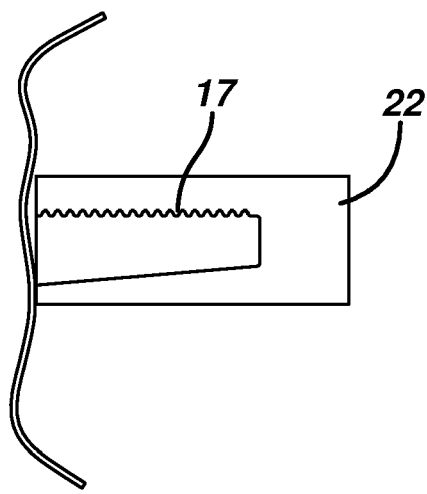
Figure 25C:
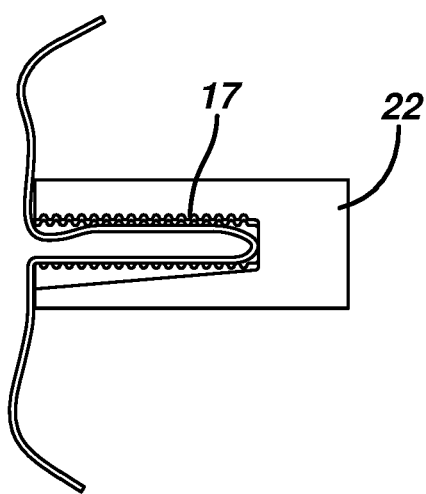
Figure 25D:
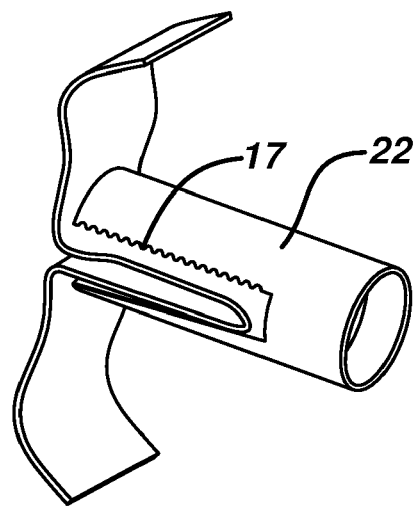

How device 20 operates within the body can be described by looking at FIGS. 25A through 25B. As shown in FIGS. 25A and 25B the end effector 22 has been placed within the body in its closed position and is placed adjacent to tissue 400. Vacuum is the applied to draw the tissue within the closed cylinder of end effector 22. Thereafter, the cylinders are rotated as shown in FIGS. 25C and 25D. Now, a clip or other fastening means such as those described above can be applied to maintain the plication. For the embodiment shown in FIG. 22, the device can now be rotated even further to pinch the tissue between the cylinders to maintain the plication. In addition Figures show the cylinders having gripping means 17 on either or both cylinders to better grip tissue therein.

The present invention has been described above with respect to its use during a transoral plication procedure. However, it should be understood that the device is also adaptable for use during laparoscopic and open tissue plication procedures without departing from the scope of the invention. Additionally, it is intended that each of the embodiments described above for the folding member be interchangeable and useable with each of the tissue fastening embodiments during a tissue plication procedure.

It is also to be understood that the above described might be sterilized and reused. There are any number of sterilization methods known to those skilled in the art including: gamma radiation and ETO.

While preferred embodiments of the present invention have been shown and described herein, it will be obvious to those skilled in the art that such embodiments are provided by way of example only. Numerous variations, changes, and substitutions will now occur to those skilled in the art without departing from the spirit and scope of the appended claims.

What is claimed is:

1. A device for maintaining a plication within a hollow organ, said device comprising:
  a. an elongated member having distal and proximal ends, said distal end is for insertion into a body cavity, said elongated member having an end effector at said distal end, said end effector comprising an outer cylinder having at least one opening in a cylindrical wall thereof, and an inner cylinder having at least one opening in a cylindrical wall thereof, said inner cylinder is at least partially disposed within said outer cylinder, wherein said cylinders are rotatable with respect to each other to pinch the tissue between the cylinders to maintain the plication and wherein said end effector is detachable from said elongated member such that it can remain within said body cavity; and
  b. a tubular channel running through said elongated member which is in fluid communication with said end effector, said channel having a vacuum source attached at a proximal end thereof.

2. The device of claim 1 wherein said outer cylinder further includes a tissue gripping means along an outer edge of said aperture.

3. The device of claim 1 wherein said inner cylinder further includes a tissue gripping means along an outer edge of said aperture.

4. The device of claim 3 wherein, said outer cylinder has a pair of openings in said cylindrical wall, and said an inner cylinder has a pair of openings in said cylindrical wall, said inner cylinder is at least partially disposed within said outer cylinder such that said aperture on said outer cylinder at least partially overlaps an aperture on said inner cylinder.

5. The device of claim 1 wherein said elongated member is an endoscope.

6. The device of claim 1 wherein said elongated member further comprises a vacuum source in communication with said end effector.

7. The device according to claim 1 further including a visualization device.

* * * * *